(12) United States Patent
Homma et al.

(10) Patent No.: US 9,243,071 B2
(45) Date of Patent: Jan. 26, 2016

(54) FUSION PROTEIN FOR SUPPRESSION OF AUTOANTIBODIES

(75) Inventors: Masayuki Homma, Narita (JP); Takahisa Kogure, Narita (JP); Kenji Nakajima, Izumisano (JP)

(73) Assignee: Nihon Pharmaceutical Co., Ltd, Tokyo (JP)

( * ) Notice: Subject to any disclaimer, the term of this patent is extended or adjusted under 35 U.S.C. 154(b) by 82 days.

(21) Appl. No.: 14/110,287

(22) PCT Filed: Apr. 2, 2012

(86) PCT No.: PCT/JP2012/058912
§ 371 (c)(1),
(2), (4) Date: Oct. 7, 2013

(87) PCT Pub. No.: WO2012/141026
PCT Pub. Date: Oct. 18, 2012

(65) Prior Publication Data
US 2014/0335085 A1    Nov. 13, 2014

(30) Foreign Application Priority Data

Apr. 13, 2011 (JP) ................. 2011-088762

(51) Int. Cl.
| | |
|---|---|
| *A61K 39/00* | (2006.01) |
| *C12N 15/62* | (2006.01) |
| *C12N 15/63* | (2006.01) |
| *C07K 16/46* | (2006.01) |
| *C07K 16/42* | (2006.01) |
| *C07K 14/705* | (2006.01) |
| *A61K 38/00* | (2006.01) |

(52) U.S. Cl.
CPC .............. *C07K 16/42* (2013.01); *C07K 14/705* (2013.01); *A61K 38/00* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| 2007/0253966 A1 | 11/2007 | Glaesner et al. |
| 2012/0123099 A1 | 5/2012 | Homma |

FOREIGN PATENT DOCUMENTS

| DE | 101 60 248 A1 | 6/2003 |
| JP | 09-077800 A | 3/1997 |
| JP | 2007-505643 A | 3/2007 |
| JP | 4495776 B1 | 7/2010 |
| WO | 03/068822 A2 | 8/2003 |
| WO | 2004/110472 A2 | 12/2004 |
| WO | 2011/013470 A1 | 2/2011 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Ting Chang, et al., "Selective recognition and elimination of nicotinic acetylcholine receptor-reactive B cells by a recombinant fusion protein AChR-Fc in myasthenia gravis in vitro", Journal of Neuroimmunology, Elsevier Science Publishers BV, NL, vol. 227, No. 1-2, Oct. 8, 2010, pp. 35-43.
Zocher, et al., "Specific Depletion of Autoreactive B Lymphocytes by a Recombinant Fusion Protein In Vitro and In Vivo"; International Immunology, Oxford University Press, GB, vol. 15, No. 7, Jul. 1, 2003, pp. 789-796.
Supplementary European Search Report for EP12 77 0896, Nov. 2014.
Zocher et al., "Specific depletion of autoreactive B lymphocytes by recombinant fusion protein in vitro and in vivo", International Immunology, 2003 vol. 15, No. 7, pp. 789-796.
Tsouloufis et al., "Reconstitution of conformationally dependent epitopes on the N-terminal extracellular domain of the human muscle acetylcholine receptor alpha subunit expressed in *Escherichia coli*: implications for myasthenia gravis therapeutic approaches", International Immunology, 2000 vol. 12, No. 9, pp. 1255-1265.
International Search Report for PCT/JP2012/058912, Nov. 2014.
Koji Abe, "Trends of clinical test studies for myasthenia gravis", Nippon Rinsho, 2008-6, vol. 66, No. 6, pp. 1155-1157 (English Abstract).
Susumu Kusunoki, "High-dose therapy by immunoglobulin", Shinkei Ciryo, 2008, vol. 25, No. 6, pp. 689-692.
Report of 1995 by the Search and Study Team for Special Diseases and Immunological Neural Diseases, Japanese Health and Welfare Ministry, "Guideline for the Treatment of Myasthenia gravis (MG)" pp. 1-30 (English Abstract).
Report on the Current Status of Treatment and Prognosis of Myasthenia Gravis in Japan, Memorial Lecture at the Fourth MG Forum, held on Jun. 13, 2004, in Tokyo Grand Hotel located at 2-5-2, Shiba, Minato-ku, Tokyo 105-0014, Japan, pp. 1-15, (English Abstract).

* cited by examiner

*Primary Examiner* — Christine J Saoud
*Assistant Examiner* — Jon M Lockard
(74) *Attorney, Agent, or Firm* — Nelson Mullins Riley & Scarborough LLP; Susan S. Jackson, Esq.; Jeanne M. DiGiorgio, Esq.

(57) ABSTRACT

A new fusion protein which can specifically suppress the autoantibodies, which can effectively prevent or treat the autoimmune disease of autoantibody type, and which can be expressed in an amount sufficient for industrial production. A fusion protein, characterized in that, a protein (X) containing a site recognized by autoantibodies which are a cause of the autoimmune disease of autoantibody type is connected to a protein (A) containing a fragment of the antibody heavy chain constant region which exhibits the antibody-dependent cellular cytotoxicity with a linker peptide (L) consisting of one or more amino acid(s), wherein the protein (X), the linker peptide (L) and the protein (A) are connected in this order by means of peptide bond from N terminal to C terminal.

10 Claims, 6 Drawing Sheets

Fig. 8B a1-L-Fc

SEQUENCE LISTING

<160> NUMBER OF SEQ ID NOS: 32

<210> SEQ ID NO 1
<211> LENGTH: 1413
<212> TYPE: DNA
<213> ORGANISM: homo sapiens

<400> SEQUENCE: 1

```
aagcttgccg ccaccatgga gccctggcct ctcctcctgc tctttagcct ttgctcagct    60
ggcctcgtcc tgggctccga acatgagacc cgtctggtgg caaagctatt taaagactac   120
agcagcgtgg tgcggccagt ggaagaccac cgccaggtcg tggaggtcac cgtgggcctg   180
cagctgatac agctcatcaa tgtggatgaa gtaaatcaga tcgtgacaac caatgtgcgt   240
ctgaaacagc aatgggtgga ttacaaccta aatggaatc cagatgacta tggcggtgtg   300
aaaaaaattc acattccttc agaaaagatc tggcgcccag accttgttct ctataacaat   360
gcagatggtg actttgctat tgtcaagttc accaaagtgc tcctgcagta cactggccac   420
atcacgtgga cacctccagc catctttaaa agctactgtg agatcatcgt cacccacttt   480
cccttttgatg aacagaactg cagcatgaag ctgggcacct ggacctacga cggctctgtc   540
gtggccatca acccggaaag cgaccagcca gacctgagca acttcatgga gagcggggag   600
tgggtgatca aggagtcccg gggctggaag cactccgtga cctattcctg ctgccccgac   660
accccctacc tggacatcac ctaccacttc gtcatgcagc gcctggagcc caaatcttgt   720
gacaaaactc acacatgccc accgtgccca gcacctgaac tcctgggggg accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggatga gctgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctcccctgt ctccgggtaa atgataagaa ttc                              1413
```

<210> SEQ ID NO 2
<211> LENGTH: 442
<212> TYPE: PRT
<213> ORGANISM: homo sapiens

<400> SEQUENCE: 2

```
Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
                20                  25                  30

Val Gly Leu Gln Leu Ile Gln Leu Ile Asn Val Asp Glu Val Asn Gln
            35                  40                  45

Ile Val Thr Thr Asn Val Arg Leu Lys Gln Gln Trp Val Asp Tyr Asn
        50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asn Ala
                85                  90                  95

Asp Gly Asp Phe Ala Ile Val Lys Phe Thr Lys Val Leu Leu Gln Tyr
            100                 105                 110
```

```
Thr Gly His Ile Thr Trp Thr Pro Pro Ala Ile Phe Lys Ser Tyr Cys
        115                 120                 125
Glu Ile Ile Val Thr His Phe Pro Phe Asp Glu Gln Asn Cys Ser Met
    130                 135                 140
Lys Leu Gly Thr Trp Thr Tyr Asp Gly Ser Val Val Ala Ile Asn Pro
145                 150                 155                 160
Glu Ser Asp Gln Pro Asp Leu Ser Asn Phe Met Glu Ser Gly Glu Trp
                165                 170                 175
Val Ile Lys Glu Ser Arg Gly Trp Lys His Ser Val Thr Tyr Ser Cys
                180                 185                 190
Cys Pro Asp Thr Pro Tyr Leu Asp Ile Thr Tyr His Phe Val Met Gln
        195                 200                 205
Arg Leu Glu Pro Lys Ser Cys Asp Lys Thr His Thr Cys Pro Pro Cys
    210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
                260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
        340                 345                 350
Leu Thr Lys Asn Gln Val Ser Leu Thr Cys Leu Val Lys Gly Phe Tyr
    355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
        420                 425                 430
Gln Lys Ser Leu Ser Leu Ser Pro Gly Lys
        435                 440

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
cccaagcttg ccgccaccat ggag                                          24

<210> SEQ ID NO 4
<211> LENGTH: 81
```

```
<212> TYPE: DNA
<213> ORGANISM: Artificial Sequence
<220> FEATURE:
<223> OTHER INFORMATION: Primer

<400> SEQUENCE: 4
gctcttaggc tccgatccgc caccgccaga gccacctccg cctgaaccgc ctccaccggg    60
cagccgttgc atgacgaagt g                                             81

<210> SEQ ID NO 5
<211> LENGTH: 768
<212> TYPE: DNA
<213> ORGANISM: homo sapiens

<400> SEQUENCE: 5
cccaagcttg ccgccaccat ggagccatgg cccctgctcc ttcttttcag cctgtgttca    60
gctggcctcg tgctgggcag cgagcacgaa accaggttgg tcgctaaact tttcaaagat   120
tactcctcag tagtgaggcc tgtagaggat catcggcagg tggtggaggt cactgtggga   180
ctccagctca tccagttgat caatgtcgat gaggtcaacc aaatcgtcac cactaatgtc   240
cgactgaagc agcagtgggt cgactacaac ctgaagtgga atcccgatga ctacggtggt   300
gtgaaaaaaa tacatattcc cagtgagaag atctggcgtc cagatcttgt tctgtacaac   360
aacgctgatg agatttcgc tatcgtcaag ttcaccaaag tgctgctgca gtatacaggt   420
catataactt ggactccccc agcaatcttt aagagttact gcgagatcat agtgacccat   480 tttcccttg acgagcagaa ttgttccatg aagctgggca cttggaccta cgacgggtct   540
gtcgtggcta ttaatccaga aagcgatcag cccgatcttt caaattttat ggagtccggt   600
gagtgggtga tcaaagaatc aaggggggtgg aaacattcag tgacctactc ttgctgtcct   660
gatactccct acctcgacat tacctaccac ttcgtcatgc aacggctgcc cggtggaggc   720
ggttcaggcg gaggtggctc tggcggtggc ggatcggagc ctaagagc                768

<210> SEQ ID NO 6
<211> LENGTH: 82
<212> TYPE: DNA
<213> ORGANISM: Artificial Sequence
<220> FEATURE:
<223> OTHER INFORMATION: Primer

<400> SEQUENCE: 6
caacggctgc ccggtggagg cggttcaggc ggaggtggct ctggcggtgg cggatcggag    60
cctaagagct gcgataaaac ac                                            82

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ggaattctta tcatttacct g                                             21

<210> SEQ ID NO 8
<211> LENGTH: 766
<212> TYPE: DNA
<213> ORGANISM: homo sapiens

<400> SEQUENCE: 8
```

| | |
|---|---:|
| caacggctgc ccggtggagg cggttcaggc ggaggtggct ctggcggtgg cggatcggag | 60 |
| cctaagagct gcgataaaac acacacatgc cctccctgcc ccgctccaga gctgttgggc | 120 |
| ggaccaagcg ttttcctgtt cccaccaaag cccaaggaca ctttgatgat ctctcggact | 180 |
| cctgaagtga catgcgtcgt ggtagatgtc tctcatgaag atccagaggt gaaatttaac | 240 |
| tggtatgtag acggcgtgga ggtgcacaat gccaaaacca gcctcgaga agaacagtac | 300 |
| aatagtacat accgagtggt ttctgttttg accgtgcttc accaggactg gctgaacgga | 360 |
| aaggaataca aatgcaaggt ctcaaacaag gcattgccag cccccatcga aagacaatt | 420 |
| tctaaagcca aggacagcc cagagagcct caggtgtata ccctcccacc atcacgagac | 480 |
| gaactcacaa aaaaccaggt ttccctcacc tgtctggtga aggggtttta cccatctgat | 540 |
| atcgccgtcg aatgggagtc taacggacag cctgagaata attataagac aactccacct | 600 |
| gtcctggaca gtgatggatc tttctttctg tacagtaaac tgaccgtgga taagtcacgc | 660 |
| tggcaacaag gtaatgtgtt cagctgcagc gtcatgcacg aggctctgca taaccattat | 720 |
| acacagaagt cactctctct gtccccaggt aaatgataag aattcc | 766 |

<210> SEQ ID NO 9
<211> LENGTH: 1465
<212> TYPE: DNA
<213> ORGANISM: homo sapiens

<400> SEQUENCE: 9

| | |
|---|---:|
| cccaagcttg ccgccaccat ggagccatgg cccctgctcc ttcttttcag cctgtgttca | 60 |
| gctggcctcg tgctgggcag cgagcacgaa accaggttgg tcgctaaact tttcaaagat | 120 |
| tactcctcag tagtgaggcc tgtagaggat catcggcagg tggtggaggt cactgtggga | 180 |
| ctccagctca tccagttgat caatgtcgat gaggtcaacc aaatcgtcac cactaatgtc | 240 |
| cgactgaagc agcagtgggt cgactacaac ctgaagtgga atcccgatga ctacggtggt | 300 |
| gtgaaaaaaa tacatattcc cagtgagaag atctggcgtc cagatcttgt tctgtacaac | 360 |
| aacgctgatg gagatttcgc tatcgtcaag ttcaccaaag tgctgctgca gtatacaggt | 420 |
| catataactt ggactccccc agcaatcttt aagagttact gcgagatcat agtgacccat | 480 |
| tttcccttg acgagcagaa ttgttccatg aagctgggca cttggaccta cgacgggtct | 540 |
| gtcgtggcta ttaatccaga aagcgatcag cccgatcttt caaattttat ggagtccggt | 600 |
| gagtgggtga tcaaagaatc aaggggggtgg aaacattcag tgacctactc ttgctgtcct | 660 |
| gatactcccct acctcgacat tacctaccac ttcgtcatgc aacggctgcc cggtggaggc | 720 |
| ggttcaggcg gaggtggctc tggcggtggc ggatcggagc ctaagagctg cgataaaaca | 780 |
| cacacatgcc ctccctgccc cgctccagag ctgttgggcg gaccaagcgt tttcctgttc | 840 |
| ccaccaaagc ccaaggacac tttgatgatc tctcggactc ctgaagtgac atgcgtcgtg | 900 |
| gtagatgtct ctcatgaaga tccagaggtg aaatttaact ggtatgtaga cggcgtggag | 960 |
| gtgcacaatg ccaaaaccaa gcctcgagaa gaacagtaca atagtacata ccgagtggtt | 1020 |
| tctgttttga ccgtgcttca ccaggactgg ctgaacggaa aggaatacaa atgcaaggtc | 1080 |
| tcaaacaagg cattgccagc ccccatcgaa agacaatttc taaagccaa ggacagccc | 1140 |
| agagagcctc aggtgtatac cctcccacca tcacgagacg aactcacaaa aaaccaggtt | 1200 |
| tccctcacct gtctggtgaa ggggttttac ccatctgata tcgccgtcga atgggagtct | 1260 |
| aacggacagc ctgagaataa ttataagaca actccacctg tcctggacag tgatggatc | 1320 |
| ttctttctgt acagtaaact gaccgtggat aagtcacgct ggcaacaagg taatgtgttc | 1380 |

```
agctgcagcg tcatgcacga ggctctgcat aaccattata cacagaagtc actctctctg    1440
tccccaggta aatgataaga attcc                                          1465

<210> SEQ ID NO 10
<211> LENGTH: 458
<212> TYPE: PRT
<213> ORGANISM: homo sapiens

<400> SEQUENCE: 10

Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile Gln Leu Ile Asn Val Asp Glu Val Asn Gln
        35                  40                  45

Ile Val Thr Thr Asn Val Arg Leu Lys Gln Gln Trp Val Asp Tyr Asn
    50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asn Ala
                85                  90                  95

Asp Gly Asp Phe Ala Ile Val Lys Phe Thr Lys Val Leu Leu Gln Tyr
            100                 105                 110

Thr Gly His Ile Thr Trp Thr Pro Pro Ala Ile Phe Lys Ser Tyr Cys
        115                 120                 125

Glu Ile Ile Val Thr His Phe Pro Phe Asp Glu Gln Asn Cys Ser Met
    130                 135                 140

Lys Leu Gly Thr Trp Thr Tyr Asp Gly Ser Val Val Ala Ile Asn Pro
145                 150                 155                 160

Glu Ser Asp Gln Pro Asp Leu Ser Asn Phe Met Glu Ser Gly Glu Trp
                165                 170                 175

Val Ile Lys Glu Ser Arg Gly Trp Lys His Ser Val Thr Tyr Ser Cys
            180                 185                 190

Cys Pro Asp Thr Pro Tyr Leu Asp Ile Thr Tyr His Phe Val Met Gln
        195                 200                 205

Arg Leu Pro Gly Gly Gly Ser Gly Gly Gly Ser Gly Gly Gly
    210                 215                 220

Gly Ser Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350
```

```
Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
    450                 455

<210> SEQ ID NO 11
<211> LENGTH: 330
<212> TYPE: PRT
<213> ORGANISM: homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 330
<212> TYPE: PRT
<213> ORGANISM: homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr

```
                305                 310                 315                 320
Gln Lys Ser Leu Ser Leu Ser Pro Gly Lys
                325                 330

<210> SEQ ID NO 13
<211> LENGTH: 437
<212> TYPE: PRT
<213> ORGANISM: homo sapiens

<400> SEQUENCE: 13

Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile Gln Leu Ile Asn Val Asp Glu Val Asn Gln
        35                  40                  45

Ile Val Thr Thr Asn Val Arg Leu Lys Gln Gln Trp Val Asp Tyr Asn
    50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asn Ala
                85                  90                  95

Asp Gly Asp Phe Ala Ile Val Lys Phe Thr Lys Val Leu Leu Gln Tyr
            100                 105                 110

Thr Gly His Ile Thr Trp Thr Pro Pro Ala Ile Phe Lys Ser Tyr Cys
        115                 120                 125

Glu Ile Ile Val Thr His Phe Pro Phe Asp Glu Gln Asn Cys Ser Met
    130                 135                 140

Lys Leu Gly Thr Trp Thr Tyr Asp Gly Ser Val Val Ala Ile Asn Pro
145                 150                 155                 160

Glu Ser Asp Gln Pro Asp Leu Ser Asn Phe Met Glu Ser Gly Glu Trp
                165                 170                 175

Val Ile Lys Glu Ser Arg Gly Trp Lys His Ser Val Thr Tyr Ser Cys
            180                 185                 190

Cys Pro Asp Thr Pro Tyr Leu Asp Ile Thr Tyr His Phe Val Met Gln
        195                 200                 205

Arg Leu Pro Leu Tyr Phe Ile Val Asn Val Ile Ile Pro Cys Leu Leu
    210                 215                 220

Phe Ser Phe Leu Thr Gly Leu Val Phe Tyr Leu Pro Thr Asp Ser Gly
225                 230                 235                 240

Glu Lys Met Thr Leu Ser Ile Ser Val Leu Leu Ser Leu Thr Val Phe
                245                 250                 255

Leu Leu Val Ile Val Glu Leu Ile Pro Ser Thr Ser Ser Ala Val Pro
            260                 265                 270

Leu Ile Gly Lys Tyr Met Leu Phe Thr Met Val Phe Val Ile Ala Ser
        275                 280                 285

Ile Ile Ile Thr Val Ile Val Ile Asn Thr His His Arg Ser Pro Ser
    290                 295                 300

Thr His Val Met Pro Asn Trp Val Arg Lys Val Phe Ile Asp Thr Ile
305                 310                 315                 320

Pro Asn Ile Met Phe Phe Ser Thr Met Lys Arg Pro Ser Arg Glu Lys
                325                 330                 335

Gln Asp Lys Lys Ile Phe Thr Glu Asp Ile Asp Ile Ser Asp Ile Ser
            340                 345                 350
```

```
Gly Lys Pro Gly Pro Pro Met Gly Phe His Ser Pro Leu Ile Lys
            355                 360                 365

His Pro Glu Val Lys Ser Ala Ile Glu Gly Ile Lys Tyr Ile Ala Glu
    370                 375                 380

Thr Met Lys Ser Asp Gln Glu Ser Asn Asn Ala Ala Ala Glu Trp Lys
385                 390                 395                 400

Tyr Val Ala Met Val Met Asp His Ile Leu Leu Gly Val Phe Met Leu
                405                 410                 415

Val Cys Ile Ile Gly Thr Leu Ala Val Phe Ala Gly Arg Leu Ile Glu
            420                 425                 430

Leu Asn Gln Gln Gly
        435

<210> SEQ ID NO 14
<211> LENGTH: 462
<212> TYPE: PRT
<213> ORGANISM: homo sapiens

<400> SEQUENCE: 14

Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile Gln Leu Ile Asn Val Asp Glu Val Asn Gln
        35                  40                  45

Ile Val Thr Thr Asn Val Arg Leu Lys Gln Gly Asp Met Val Asp Leu
    50                  55                  60

Pro Arg Pro Ser Cys Val Thr Leu Gly Val Pro Leu Phe Ser His Leu
65                  70                  75                  80

Gln Asn Glu Gln Trp Val Asp Tyr Asn Leu Lys Trp Asn Pro Asp Asp
                85                  90                  95

Tyr Gly Gly Val Lys Lys Ile His Ile Pro Ser Glu Lys Ile Trp Arg
            100                 105                 110

Pro Asp Leu Val Leu Tyr Asn Asn Ala Asp Gly Asp Phe Ala Ile Val
        115                 120                 125

Lys Phe Thr Lys Val Leu Leu Gln Tyr Thr Gly His Ile Thr Trp Thr
130                 135                 140

Pro Pro Ala Ile Phe Lys Ser Tyr Cys Glu Ile Ile Val Thr His Phe
145                 150                 155                 160

Pro Phe Asp Glu Gln Asn Cys Ser Met Lys Leu Gly Thr Trp Thr Tyr
                165                 170                 175

Asp Gly Ser Val Val Ala Ile Asn Pro Glu Ser Asp Gln Pro Asp Leu
            180                 185                 190

Ser Asn Phe Met Glu Ser Gly Glu Trp Val Ile Lys Glu Ser Arg Gly
        195                 200                 205

Trp Lys His Ser Val Thr Tyr Ser Cys Cys Pro Asp Thr Pro Tyr Leu
210                 215                 220

Asp Ile Thr Tyr His Phe Val Met Gln Arg Leu Pro Leu Tyr Phe Ile
225                 230                 235                 240

Val Asn Val Ile Ile Pro Cys Leu Leu Phe Ser Phe Leu Thr Gly Leu
                245                 250                 255

Val Phe Tyr Leu Pro Thr Asp Ser Gly Glu Lys Met Thr Leu Ser Ile
            260                 265                 270

Ser Val Leu Leu Ser Leu Thr Val Phe Leu Leu Val Ile Val Glu Leu
        275                 280                 285
```

```
Ile Pro Ser Thr Ser Ser Ala Val Pro Leu Ile Gly Lys Tyr Met Leu
    290                 295                 300

Phe Thr Met Val Phe Val Ile Ala Ser Ile Ile Thr Val Ile Val
305                 310                 315                 320

Ile Asn Thr His His Arg Ser Pro Ser Thr His Val Met Pro Asn Trp
                325                 330                 335

Val Arg Lys Val Phe Ile Asp Thr Ile Pro Asn Ile Met Phe Phe Ser
            340                 345                 350

Thr Met Lys Arg Pro Ser Arg Glu Lys Gln Asp Lys Lys Ile Phe Thr
        355                 360                 365

Glu Asp Ile Asp Ile Ser Asp Ile Ser Gly Lys Pro Gly Pro Pro Pro
    370                 375                 380

Met Gly Phe His Ser Pro Leu Ile Lys His Pro Glu Val Lys Ser Ala
385                 390                 395                 400

Ile Glu Gly Ile Lys Tyr Ile Ala Glu Thr Met Lys Ser Asp Gln Glu
                405                 410                 415

Ser Asn Asn Ala Ala Ala Glu Trp Lys Tyr Val Ala Met Val Met Asp
            420                 425                 430

His Ile Leu Leu Gly Val Phe Met Leu Val Cys Ile Ile Gly Thr Leu
        435                 440                 445

Ala Val Phe Ala Gly Arg Leu Ile Glu Leu Asn Gln Gln Gly
    450                 455                 460

<210> SEQ ID NO 15
<211> LENGTH: 457
<212> TYPE: PRT
<213> ORGANISM: homo sapiens

<400> SEQUENCE: 15

Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile Gln Leu Ile Asn Val Asp Glu Val Asn Gln
        35                  40                  45

Ile Val Thr Thr Asn Val Arg Leu Lys Gln Gln Trp Val Asp Tyr Asn
    50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asn Ala
                85                  90                  95

Asp Gly Asp Phe Ala Ile Val Lys Phe Thr Lys Val Leu Leu Gln Tyr
            100                 105                 110

Thr Gly His Ile Thr Trp Thr Pro Pro Ala Ile Phe Lys Ser Tyr Cys
        115                 120                 125

Glu Ile Ile Val Thr His Phe Pro Phe Asp Glu Gln Asn Cys Ser Met
    130                 135                 140

Lys Leu Gly Thr Trp Thr Tyr Asp Gly Ser Val Val Ala Ile Asn Pro
145                 150                 155                 160

Glu Ser Asp Gln Pro Asp Leu Ser Asn Phe Met Glu Ser Gly Glu Trp
                165                 170                 175

Val Ile Lys Glu Ser Arg Gly Trp Lys His Ser Val Thr Tyr Ser Cys
            180                 185                 190

Cys Pro Asp Thr Pro Tyr Leu Asp Ile Thr Tyr His Phe Val Met Gln
```

```
                195                 200                 205
Arg Leu Gly Gly Gly Ser Gly Gly Gly Ser Gly Gly Gly
    210                 215                 220

Ser Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 16
<211> LENGTH: 78
<212> TYPE: DNA
<213> ORGANISM: Artificial Sequence
<220> FEATURE:
<223> OTHER INFORMATION: Primer

<400> SEQUENCE: 16
gctcttaggc tccgatccgc caccgccaga gccacctccg cctgaaccgc ctccacccag     60
ccgttgcatg acgaagtg                                                  78

<210> SEQ ID NO 17
<211> LENGTH: 79
<212> TYPE: DNA
<213> ORGANISM: Artificial Sequence
<220> FEATURE:
<223> OTHER INFORMATION: Primer

<400> SEQUENCE: 17
caacggctgg gtggaggcgg ttcaggcgga ggtggctctg gcggtggcgg atcggagcct     60
aagagctgcg ataaaacac                                                 79
```

<210> SEQ ID NO 18
<211> LENGTH: 1462
<212> TYPE: DNA
<213> ORGANISM: homo sapiens

<400> SEQUENCE: 18

```
cccaagcttg ccgccaccat ggagccatgg cccctgctcc ttcttttcag cctgtgttca      60
gctggcctcg tgctgggcag cgagcacgaa accaggttgg tcgctaaact tttcaaagat     120
tactcctcag tagtgaggcc tgtagaggat catcggcagg tggtggaggt cactgtggga     180
ctccagctca tccagttgat caatgtcgat gaggtcaacc aaatcgtcac cactaatgtc     240
cgactgaagc agcagtgggt cgactacaac ctgaagtgga atcccgatga ctacggtggt     300
gtgaaaaaaa tacatattcc cagtgagaag atctggcgtc cagatcttgt tctgtacaac     360
aacgctgatg gagatttcgc tatcgtcaag ttcaccaaag tgctgctgca gtatacaggt     420
catataactt ggactccccc agcaatcttt aagagttact gcgagatcat agtgacccat     480
tttcccttg acgagcagaa ttgttccatg aagctgggca cttggaccta cgacgggtct     540
gtcgtggcta ttaatccaga aagcgatcag cccgatcttt caaattttat ggagtccggt     600
gagtgggtga tcaaagaatc aaggggggtgg aaacattcag tgacctactc ttgctgtcct     660
gatactccct acctcgacat tacctaccac ttcgtcatgc aacggctggg tggaggcggt     720
tcaggcggag gtggctctgg cggtggcgga tcggagccta agagctgcga taaaacacac     780
acatgccctc cctgccccgc tccagagctg ttgggcggac aagcgttttt cctgttccca     840
ccaaagccca aggacacttt tgatgatctct cggactcctg aagtgacatg cgtcgtggta     900
gatgtctctc atgaagatcc agaggtgaaa tttaactggt atgtagacgg cgtggaggtg     960
cacaatgcca aaaccaagcc tcgagaagaa cagtacaata gtacataccg agtggttct    1020
gttttgaccg tgcttcacca ggactggctg aacggaaagg aatacaaatg caaggtctca    1080
aacaaggcat gccagccccc catcgaaaag acaatttcta agccaaagg acagcccaga    1140
gagcctcagg tgtataccct cccaccatca cgagacgaac tcacaaaaaa ccaggtttcc    1200
ctcacctgtc tggtgaaggg gttttaccca tctgatatcg ccgtcgaatg ggagtctaac    1260
ggacagcctg agaataatta taagacaact ccacctgtcc tggacagtga tggatctttc    1320
tttctgtaca gtaaactgac cgtggataag tcacgctggc aacaaggtaa tgtgttcagc    1380
tgcagcgtca tgcacgaggc tctgcataac cattatacac agaagtcact ctctctgtcc    1440
ccaggtaaat gataagaatt cc                                             1462
```

<210> SEQ ID NO 19
<211> LENGTH: 457
<212> TYPE: PRT
<213> ORGANISM: homo sapiens

<400> SEQUENCE: 19

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly
225                 230                 235                 240

Gly Ser Gly Gly Gly Ser Ser Glu His Glu Thr Arg Leu Val Ala
                245                 250                 255

Lys Leu Phe Lys Asp Tyr Ser Ser Val Val Arg Pro Val Glu Asp His
            260                 265                 270

Arg Gln Val Val Glu Val Thr Val Gly Leu Gln Leu Ile Gln Leu Ile
        275                 280                 285

Asn Val Asp Glu Val Asn Gln Ile Val Thr Thr Asn Val Arg Leu Lys
    290                 295                 300

Gln Gln Trp Val Asp Tyr Asn Leu Lys Trp Asn Pro Asp Asp Tyr Gly
305                 310                 315                 320

Gly Val Lys Lys Ile His Ile Pro Ser Glu Lys Ile Trp Arg Pro Asp
                325                 330                 335

Leu Val Leu Tyr Asn Asn Ala Asp Gly Asp Phe Ala Ile Val Lys Phe
            340                 345                 350

Thr Lys Val Leu Leu Gln Tyr Thr Gly His Ile Thr Trp Thr Pro Pro
        355                 360                 365

Ala Ile Phe Lys Ser Tyr Cys Glu Ile Ile Val Thr His Phe Pro Phe
    370                 375                 380

Asp Glu Gln Asn Cys Ser Met Lys Leu Gly Thr Trp Thr Tyr Asp Gly
385                 390                 395                 400

Ser Val Val Ala Ile Asn Pro Glu Ser Asp Gln Pro Asp Leu Ser Asn
                405                 410                 415

Phe Met Glu Ser Gly Glu Trp Val Ile Lys Glu Ser Arg Gly Trp Lys
            420                 425                 430

His Ser Val Thr Tyr Ser Cys Cys Pro Asp Thr Pro Tyr Leu Asp Ile
        435                 440                 445

Thr Tyr His Phe Val Met Gln Arg Leu
    450                 455

<210> SEQ ID NO 20
<211> LENGTH: 2
<212> TYPE: PRT
<213> ORGANISM: Artificial Sequence
<220> FEATURE:
```

```
<223> OTHER INFORMATION: Peptide Linker

<400> SEQUENCE: 20

Gly Ser
1

<210> SEQ ID NO 21
<211> LENGTH: 2
<212> TYPE: PRT
<213> ORGANISM: Artificial Sequence
<220> FEATURE:
<223> OTHER INFORMATION: Peptide Linker

<400> SEQUENCE: 21

Ser Gly
1

<210> SEQ ID NO 22
<211> LENGTH: 5
<212> TYPE: PRT
<213> ORGANISM: Artificial Sequence
<220> FEATURE:
<223> OTHER INFORMATION: Peptide Linker
<220> FEATURE:
<223> OTHER INFORMATION: This sequence may be repeated one to eight
      times.

<400> SEQUENCE: 22

Gly Gly Gly Gly Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide Linker
<220> FEATURE:
<223> OTHER INFORMATION: The second to sixth amino acids may be repeated
      one to eight times.

<400> SEQUENCE: 23

Pro Gly Gly Gly Gly Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide Linker
<220> FEATURE:
<223> OTHER INFORMATION: The third to seventh amino acids may be
      repeated one to eight times.

<400> SEQUENCE: 24

Gly Ser Gly Gly Gly Gly Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Peptide Linker
<220> FEATURE:
<223> OTHER INFORMATION: This sequence may be repeated one to eight
      times.
```

```
<400> SEQUENCE: 25

Ser Ser Ser Ser Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide Linker
<220> FEATURE:
<223> OTHER INFORMATION: The first to fifth amino acids may be repeated
      one to eight times.

<400> SEQUENCE: 26

Ser Ser Ser Ser Gly Ser Pro
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide Linker

<400> SEQUENCE: 27

Gly Gly Ser Ser Arg Gly Gly
1               5

<210> SEQ ID NO 28
<211> LENGTH: 18
<212> TYPE: PRT
<213> ORGANISM: Artificial Sequence
<220> FEATURE:
<223> OTHER INFORMATION: Peptide Linker

<400> SEQUENCE: 28

Gly Gly Ser Ser Arg Ser Ser Ser Ser Gly Gly Gly Gly Ser Gly Gly
1               5                   10                  15

Gly Gly

<210> SEQ ID NO 29
<211> LENGTH: 7
<212> TYPE: PRT
<213> ORGANISM: Artificial Sequence
<220> FEATURE:
<223> OTHER INFORMATION: Peptide Linker

<400> SEQUENCE: 29

Glu Phe Gly Gly Gly Gly Gly
1               5

<210> SEQ ID NO 30
<211> LENGTH: 25
<212> TYPE: PRT
<213> ORGANISM: Artificial Sequence
<220> FEATURE:
<223> OTHER INFORMATION: Peptide Linker

<400> SEQUENCE: 30

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25
```

```
<210> SEQ ID NO 31
<211> LENGTH: 14
<212> TYPE: PRT
<213> ORGANISM: Artificial Sequence
<220> FEATURE:
<223> OTHER INFORMATION: Peptide Linker

<400> SEQUENCE: 31

Asn Val Asp His Lys Pro Ser Asn Thr Lys Val Asp Lys Arg
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Peptide Linker
<220> FEATURE:
<223> OTHER INFORMATION: The second to sixth amino acids are repeated
      three times.

<400> SEQUENCE: 32

Pro Gly Gly Gly Gly Ser
1               5
```

FUSION PROTEIN FOR SUPPRESSION OF AUTOANTIBODIES

CROSS-REFERENCE TO RELATED APPLICATIONS

This application claims the benefit of Japanese Patent Application No. 2011 088762 filed on Apr. 13, 2011, which was patented as JP Patent No. 4857396 on Nov. 4, 2011, and corresponding Patent Cooperation Treaty Application No. PCT/JP2012/058912 filed on Apr. 2, 2012.

REFERENCE TO SEQUENCE LISTING

This application includes as part of its subject matter a Sequence Listing electronically submitted via EFS-Web on Oct. 7, 2013, as a single text file named "Sequence Listing.txt". The Sequence Listing Text file was created on Sep. 13, 2013 and is 38 kb in size. The contents of the Sequence Listing are hereby incorporated by reference.

FIELD OF THE INVENTION

The present invention relates to a fusion protein which can effectively prevent and treat an autoimmune disease of autoantibody type such as myasthenia gravis by neutralizing autoantibodies and inhibiting the autoantibody production. More particularly, the present invention relates to a fusion protein having necessary and sufficient strong function for prevention and treatment and also being secreted to the outside of cells as a result of expression together with keeping its stable structure whereby being able to cope even with industrial production.

BACKGROUND OF THE INVENTION

Immune system inherently has a role of recognizing and eliminating a foreign body such as bacterium or virus which is different from the self but, sometimes, it excessively reacts with one's own normal cells and tissues and attacks them due to congenital or acquired abnormality. Autoimmune disease is a general name for the diseases resulted by such a state. Among them, a disease caused by the reaction of autoantibodies (antibodies which recognize one's own cells and tissues as an antigen) with autoantigen (one's own cells and tissues) is called "autoimmune disease of autoantibody type". Examples of the autoimmune disease of autoantibody type include myasthenia gravis, hemolytic anemia of autoimmune type, idiopathic thrombocytopenic purpura, neutropenia of autoimmune type, hyperthyroidism or Hashimoto disease caused by anti-TSH antibody, acute encephalitis of autoantibody type, and non-herpetic marginal encephalitis.

As to a treating method for autoimmune disease of autoantibody type, administration of steroidal agents or immunosuppressants has been conducted frequently. However, any of those drugs does not specifically suppress the autoantibodies which are fundamental cause of the disease but generally suppress the immunoreaction as a whole. Therefore, the drugs have no specificity and the methods are not a sufficiently effective treating method in terms of QOL (Quality of Life).

With regard to myasthenia gravis which is one of the representative examples of the autoimmune diseases of autoantibody type, there is no already-known treating agent for the fundamental treatment therefor as well but merely the above steroidal agents, the above immunosuppressants, cholinesterase inhibitors, plasma exchange therapy, immunoglobulin preparations for intravenous injection, and thymectomy have been mostly used (cf. Trends of clinical test studies for myasthenia gravis, *Nippon Rinsho*, Vol. 66, No. 6, pp. 1155-1157; High-dose therapy by immunoglobulin, *Shinkei Chiryo*, Vol. 25, No. 6, pp. 689-692; "Guideline for the Treatment of Myasthenia gravis (MG)", Report of 1995 by the Search and Study Team for Special Diseases and Immunological Neural Diseases, Health and Welfare Ministry; "Current Status of Treatment and Prognosis of Myasthenia Gravis in Japan", Memorial Lecture at the Fourth MG Forum).

Among the above, the use of choline esterase inhibitors is difficult for its dose setting. Also, it may be sometimes necessary that atropine sulfate is intravenously injected or airway is secured taking the case of side effect into consideration. Moreover, when high dose is administered for a long period, its effect lowers and, in some cases, cholinergic crisis may happen, which are regarded as problematic. This agent is not intended for the therapeutic treatment but is a mere symptomatic treatment. Fundamentally, the minimum dose by which the effect is achieved is to be used and a long-term administration is to be avoided if at all possible.

With regard to steroidal agents, their side effect is regarded as problematic and control of the side effect is very important. In addition, a continued administration of such agents for a long period is difficult and it is necessary to control together with the use of nonsteroidal immunosuppressants such as tacrolims or cyclosporine. However, as mentioned already, the above agents are for mere symptomatic treatment and are not fundamental therapeutic means.

With regard to thymectomy, although it shows some effect, there are problems of anxiety of patients to excising operation and also of cost. There is another problem that it is not applicable to small children whose immune function is still undeveloped and to patients suffering from immunodeficiency disease. In addition, although it exhibits some effects, long years of up to units of ten years are required until the effect is confirmed. It is unavoidable that other symptomatic treatments are jointly conducted until the effect is acknowledged. There is still another problem that the effect was confirmed for only less than 50% of the patients.

With regard to plasma exchange therapy, a cost of as high as not less than one million yen is needed for one treatment. A subsidy for the medical expenses of myasthenia gravis according to the system for Diagnosis Procedure Combination is only about six hundred thousand yen whereby the burden at the medical care site is big. Further, there is a problem that duration of the effect thereof is as short as only about one month.

As a treating method for myasthenia gravis, effectiveness of gamma-globulin preparations have been confirmed in recent years and some pharmaceutical manufacturers are now conducting clinical tests therefor. However, since gamma-globulin preparations are biological preparations derived from human plasma, there may be a risk of infection due to unknown virus, etc. In addition, dose of the gamma-globulin preparations is high (400 mg/kg, continued administration for 5 days) and, it is expected that burdens for patients and medical care sites will be considerably high. On the other hand, duration of the effect thereof has been said to be the same as plasma exchange therapy or merely a bit longer.

To sum up, the problem in the treatment of myasthenia gravis is that, as to the treatment using low-molecular drug, it is a mere temporary symptomatic treatment and, as to plasma exchange therapy, gamma-globulin preparations and thymectomy, the problems in terms of effect and cost are still left as well.

In view of the above problems, the present inventors thought that an effective effect will be expected in a small dose causing no burden to patients if an antibody reacting only to an anti-acetylcholine receptor autoantibodies which have been believed to be a cause of myasthenia gravis can be prepared in recombinant protein. Then the present inventors prepared fusion protein of nAChRα1 subunit N-terminal extracellular region with antibody heavy chain constant region as a substitute for antiidiotype antibody in order to neutralize the anti-acetylcholine receptor autoantibodies. Since this fusion protein has the activity of neutralizing the autoantibodies and also injuring the autoantibody production cells, it has been judged to be very effective to myasthenia gravis which is one of autoimmune diseases of autoantibody type. However, this fusion protein had a low expressing amount and its industrial production was under a difficult state (cf. Japanese Patent No. 4495776).

SUMMARY OF THE INVENTION

The present invention has been created in view of the current status of the prior art as such and an object of the present invention is to provide a new fusion protein which can specifically suppress the autoantibodies, which can effectively prevent or treat the autoimmune disease of autoantibody type, and which can be expressed in an amount sufficient for industrial production. Another object of the present invention is to provide a method for manufacturing the fusion protein.

The above fusion protein in Japanese Patent No. 4495776 can be expected for its effect as a treatment agent for myasthenia gravis in two points which are inhibition of production of autoantibodies and neutralization of the produced autoantibodies. However, in the fusion protein of receptor protein with antibody heavy chain constant region, small expressing amount which is seemingly caused by steric hindrance of the structure, purity of expressed protein, etc. are the problems.

Under such circumstances, the present inventors have conducted various investigations for enhancing the expressed amount of fusion protein and the purity of expressed protein and noted that, in the fusion protein of Japanese Patent No. 4495776, each of the receptor protein and the antibody heavy chain constant region is in a complicated structure whereby, due to their steric hindrance, incorrect disulfide bond is resulted during the expression of the fusion protein and, as a result, no sufficient purity and expressed amount are achieved. As a means for solving the above, the present inventors have conceived a fusion protein wherein a flexible linker peptide is inserted between the receptor protein and the antibody heavy chain constant region. Thus, the present inventors thought that each of structures of the receptor protein and the antibody heavy chain constant region keeps the inherent stable structure by insertion of the flexible linker peptide. The present inventors then thought that, as a result of formation of stable structure in each region, a secretive effect to the outside of the cells is promoted resulting in much more production of fusion protein and, in addition, stability of fusion protein itself is enhanced whereby the proportion of the decomposed product can be made significantly small and improvement in the purity is now possible. In view of the above, the present inventors have prepared a fusion protein into which this flexible linker peptide is inserted and found that, in this fusion protein, expressed amount is greatly enhanced and purity of the expressed protein is also significantly improved as compared with the conventional fused protein having no linker peptide. The present inventors have also found that, in the fusion protein into which a flexible linker peptide is inserted, neutralizing effect for autoantibodies is significantly enhanced and the effect of specifically suppressing the autoantibody production cells is also strong as compared with the conventional fused protein having no linker peptide. The present inventors have further found that cellular cytotoxicity is more strongly achieved when the antibody heavy chain constant region (A) is positioned at the C terminal side than at the N terminal side. The present inventors have achieved the present invention on the basis of those findings.

Thus, in accordance with the present invention, there is provided a fusion protein, characterized in that, a protein (X) containing a site recognized by autoantibodies which are a cause of the autoimmune disease of autoantibody type is connected to a protein (A) containing a fragment of the antibody heavy chain constant region which exhibits the antibody-dependent cellular cytotoxicity with a linker peptide (L) consisting of one or more amino acid(s), wherein the protein (X), the linker peptide (L) and the protein (A) are connected in this order by means of peptide bond from N terminal to C terminal.

Moreover, in accordance with the present invention, there is also provided a method for manufacturing the above fusion protein which is characterized in that DNA encoding the above fusion protein is inserted into a cellular expression vector and this vector is introduced into host cells to express the fusion protein. There is further provided a composition for prevention and treatment of autoimmune disease of autoantibody type which is characterized in containing the above fusion protein as an effective ingredient.

Among the advantages of the invention, the fusion protein of the present invention neutralizes the autoantibodies existing in the body of a patient suffering from autoimmune disease of autoantibody type and also inhibits the autoantibody production whereby it can specifically suppress the autoantibodies. In addition, the fusion protein of the present invention has high expressing amount and purity and can be provided as a drug in an actual production scale. Accordingly, when the fusion protein of the present invention is used, it is now possible to effectively prevent and treat various autoimmune diseases of autoantibody type such as myasthenia gravis.

BRIEF DESCRIPTION OF THE DRAWINGS

FIG. 8B shows a binding of fusion protein α1-L-Fc to hybridoma Mab35 cells. Added concentration of the fusion protein is shown in FIG. 8B.

DETAILED DESCRIPTION OF THE INVENTION AND MODE FOR CARRYING OUT THE INVENTION

Figure 1:
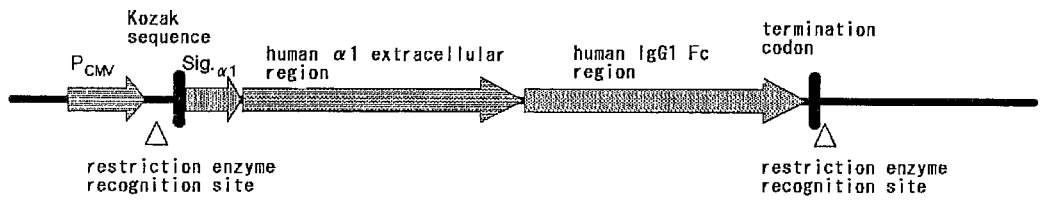
FIG. 1 is a schematic chart of region for expressing a fusion protein α1-Fc prepared in Examples.

The fusion protein of the present invention has a structure wherein a protein (X) containing a site recognized by autoantibodies which are a cause of the autoimmune disease of autoantibody type is connected to a protein (A) containing a fragment which exhibits the antibody-dependent cellular cytotoxicity of the antibody heavy chain constant region with a linker peptide (L) consisting of one or more amino acid(s).

The protein (X) corresponds to an autoantigen to autoantibodies or a part thereof and plays a role of decoy binding to autoantibodies as a substitute for the autoantigen of a patient. Thus, when the fusion protein of the present invention is administered to a patient suffering from autoimmune disease of autoantibody type, the autoantibodies in the body of the patient recognize the protein (X) part in the fusion protein as autoantigen and bind to this part. Since the bound autoantibodies cannot bind to the autoantigen which is inherently present in the body of the patient any longer, the autoantibodies can be neutralized by this method and generation of symptom of the autoimmune disease by binding of the autoantibodies to the autoantigen of the patient can be suppressed. Although the autoantibodies are not one specific antibody but are composed of a group of various antibodies, any of the antibodies is common in such a view that it has a function of recognizing the autoantigen. Accordingly, when the fusion protein of the present invention which acts as a decoy of autoantigen is used, one fusion protein can neutralize a group of various antibodies, and thus there is no need to separately prepare each fusion protein for each of various antibodies.

"Antibody" defined here stands for all of the antibody in each class of IgA, IgD, IgE, IgG an IgM and in each subclass thereof. "Antibody constant region" stands for antibody in each class or antibody in each subclass and/or a combination of antibody heavy chain constant region thereof as well. There is no particular limitation for sugar chain structure being added the antibody heavy chain constant region.

The fusion protein of the present invention contains a protein (A) which contains a fragment of the antibody heavy chain constant region in addition to a protein (X) which acts as a decoy for an autoantigen. This protein (A) also plays a role of exhibiting the antibody-dependent cellular cytotoxicity (ADCC activity). Autoantibodies are produced by B cells in the blood. Antibodies of cell surface presenting type having the same antigen binding site as the autoantibodies exist on the surface of the B cells as a B cell receptor. Accordingly, when the fusion protein of the present invention is administered to a patient, a part of the fusion protein binds to the autoantibodies in the body of the patient as mentioned above while remainder binds to the antibodies on the surface of B cells (B cell receptor) which produce the autoantibodies. When the fusion protein of the present invention binds to the B cell receptor, effector cells such as NK cell bind to a protein (A) in the fusion protein via an Fc receptor of the effector cells, exhibit the antibody-dependent cellular cytotoxicity (ADCC activity), injure the B cells binding to the fusion protein, and suppress production of autoantibodies. As such, in accordance with the present invention, the outcome is not only that the autoantibodies existing in the body are neutralized to inhibit the binding of the autoantibodies to the autoantigen but also that the specific B cells which are a production source of the autoantibodies can be selectively injured. Accordingly, the fusion protein of the present invention can prevent or treat the autoimmune disease of autoantibody type by two ways which are inhibition of the autoantibody production and neutralization of the produced autoantibodies.

The fusion protein of the present invention includes a flexible linker peptide (L) consisting of one or more amino acid(s). As a result of insertion of such a linker peptide, structure of each of the receptor protein and the antibody heavy chain constant region becomes a stable structure whereby a fusion protein becomes stable as a whole.

The present invention is characterized in that receptor protein (X), linker peptide (L) and antibody heavy chain constant region (A) are sequenced in the order of (X)-(L)-(A) from N terminal to C terminal. Theoretically, the antibody heavy chain constant region (A) is positioned in any side of N terminal side and C terminal side but the present inventors have found that an antibody heavy chain constant region (A) should be positioned in the C terminal side wherein the steric hindrance is little in binding to a receptor, for a purpose of effective achievement of antibody-dependent cellular cytotoxicity (ADCC activity) of the antibody heavy chain constant region (A). It is also presumed that, when the receptor protein (X) is positioned at N terminal, its effect as a decoy can be also strongly achieved.

The protein (X) in the fusion protein of the present invention corresponds to an autoantigen, or a part thereof, to autoantibodies which are a cause of autoimmune disease of autoantibody type in the patient to be prevented or treated. The protein (X) is decided depending upon the autoimmune disease in the patient to be prevented or treated. For example, in the case of prevention and treatment of myasthenia gravis, since myasthenia gravis is a disease resulted by such a cause that anti-nicotinic acetylcholine receptor antibodies (autoantibodies) bind, in nerve-muscle junction, to a nicotinic acetylcholine receptor (autoantigen) which is a receiver in the side of muscle of neurotransmitter acetylcholine whereby nervous/muscular transmittance by acetylcholine is inhibited, the protein (X) can be a nicotinic acetylcholine receptor which is the autoantigen. Similarly, in the case of prevention and treatment of hemolytic anemia of autoimmune type, the protein (X) can be an erythrocyte surface marker; in the case of prevention and treatment of idiopathic thrombocytopenic purpura, the protein (X) can be a platelet surface marker; in the case of prevention and treatment of neutropenia of autoimmune type, the protein (X) can be a neutrophil surface marker; in the case of prevention and treatment of hyperthyroidism or primary hypothyroidism (Hashimoto disease) caused by anti-TSH antibody, the protein (X) can be TSH; and in the case of prevention of treatment of encephalitis and encephalopathy of autoantibody type, the protein (X) can be NMDA receptor, AMPA receptor, etc.

The protein (X) is not necessary to be the whole receptor or the whole marker but may be a part thereof as far as a recognition site of autoantibodies is contained therein. For example, in the case of myasthenia gravis, the above nicotinic acetylcholine receptor is a pentameric protein consisting of four kinds of subunits and, among them, the recognition site of the autoantibodies exists in the N-terminal extracellular region of isoform 1 (an isoform expressed only in skeletal muscle and shown by SEQ ID NO:13) and isoform 2 (an isoform expressed in skeletal muscle, brain, heart, kidney and lung, and shown by SEQ ID NO:14) of an α1 subunit. Accordingly, in the case of myasthenia gravis, the protein (X) may be a nicotinic acetylcholine receptor α1 (nAChRα1) subunit or a part thereof. To be more specific, it may be isoform 1 and/or isoform 2 of nAChRα1 subunit or a part thereof and, to be still more specific, it may consists of amino acid sequence of N-terminal extracellular region of isoform 1 and/or isoform 2 of nAChRα1 subunit.

In the amino acid sequences as such, one or several (such as 1 to 20, preferably 1 to 10, and more preferably 1 to 7) amino acid(s) may be deleted, added and/or substituted as far as the homology thereof is not impaired. With regard to the range thereof, an example is amino acid sequence having 70% or more, preferably 80% or more, and more preferably 90% or more sequence identity. Homology of the amino acid sequence can be calculated using a homology calculation algorithm NCBI BLAST (National Center for Biotechnology Information Basic Local Alignment Search Tool) under such a condition that expectation value is 10, gap is allowed, matrix is BLOSUM 62 and filtering is off To be more specific, the amino acid sequence wherein deletion, addition and/or substitution as such are/is introduced can be easily prepared by substituting the corresponding DNA sequence using a commercially available kit such as Site-Directed Mutagenesis Kit (manufactured by Takara Bio Inc.) or QuickChange Site-Directed Mutagenesis Kit (manufactured by STRATAGENE). It is also possible to directly prepare the above amino acid sequence by means of an artificial gene synthesis technique.

The protein (A) in the fusion protein of the present invention is a protein containing a fragment of an antibody heavy chain constant region and it may be, for example, a Fc region of the antibody heavy chain, antibody heavy chain constant region or a part thereof. "Antibody" includes all classes of IgA, IgD, IgE, IgG and IgM and also includes all of subclasses thereof "Antibody heavy chain constant region" is a part excluding the variable region of antibody heavy chain. For example, when the class is IgG, the antibody heavy chain constant region comprises a combination of CH1 region, hinge region, CH2 region and CH3 region. The antibody heavy chain constant region may also be a combination of above each class or each subclass or heavy chain constant region thereof. For example, when the class is IgG, the Fc region of the antibody heavy chain comprises a combination of hinge region, CH2 region and CH3 region. In case of human antibody IgG1, the amino acid sequence of SEQ ID NO:11 or SEQ ID NO:12 may be specifically exemplified. Both SEQ ID NO:11 and SEQ ID NO:12 are the sequences of human antibody IgG1 Fc region. SEQ ID NO:11 is said to be a type abundantly found in Asian people while SEQ ID NO:12 is said to be a type abundantly found in European and American people.

The peptide linker (L) in the fusion protein of the present invention consists of one or more amino acid(s), preferably 5 to 45, more preferably 10 to 20, and most preferably 16 amino acids. This peptide linker may contain Gly-Ser element or Ser-Gly.

Specific examples of the peptide linker (L) include that which contains an amino acid sequence represented by
the formula (Gly-Gly-Gly-Gly-Ser)n SEQ ID NO:22,
the formula Pro-(Gly-Gly-Gly-Gly-Ser) n SEQ ID NO:23,
the formula Gly-Ser(Gly-Gly-Gly-Gly-Ser)n SEQ ID NO:24,
the formula (Ser-Ser-Ser-Ser-Gly)n SEQ ID NO:25, or
the formula (Ser-Ser-Ser-Ser-Gly)n-Ser-Pro SEQ ID NO:26
(in the formulae, n is an integer of 1 to 8).

Among the above, the amino acid sequences represented by the first and second formulae are preferred. The repetition number (n) in the formulae is preferably an integer of 1 to 4 and, more preferably, 3.

Other specific examples of the peptide linker (L) include the peptide linkers containing a sequence having a structure based on amino acid Gly and/or amino acid Ser (such as that which contains a sequence having Gly-Gly-Ser-Ser-Arg-Gly-Gly (SEQ ID NO:27), Gly-Gly-Ser-Ser-Arg-Ser-Ser-Ser-Ser-Gly-Gly-Gly-Gly-Ser-Gly-Gly-Gly-Gly (SEQ ID NO:28), or Glu-Phe-Gly-Gly-Gly-Gly-Gly (SEQ ID NO:29)).

Still other specific examples of the peptide linker (L) include those having the following amino acid sequences or containing amino acid sequences wherein improvement is applied based on those sequences.

A) Asp-Ala-Ala-Ala-Lys-Glu-Ala-Ala-Ala-Lys-Asp-Ala-Ala-Ala-Arg-Glu-Ala-Ala-Ala-Arg-Asp-Ala-Ala-Ala-Lys (SEQ ID NO: 30)

B) Asn-Val-Asp-His-Lys-Pro-Ser-Asn-Thr-Lys-Val-Asp-Lys-Arg (SEQ ID NO: 31)

A specific example of the fusion protein of the present invention is a protein consisting of amino acid sequence of SEQ ID NO:10. This fusion protein has a structure wherein the protein (X), the linker peptide (L) and the protein (A) are connected in this order by means of peptide bond from N terminal to C terminal. The protein (X) corresponds to an amino acid sequence consisting of amino acids of the 1st to 210th positions in the amino acid sequence of N-terminal extracellular region of isoform 1 of nAChRα1 subunit. The linker peptide (L) corresponds to Pro-(Gly-Gly-Gly-Gly-Ser) 3. The protein (A) corresponds to amino acid sequence of SEQ ID NO:11. In this amino acid sequence of the fusion protein, as mentioned above, one or several (such as 1 to 20, preferably 1 to 10, more preferably 1 to 7, and most preferably 1 to 3) amino acid(s) may be deleted, added and/or substituted as far as the homology thereof is not impaired.

The fusion protein of the present invention can be manufactured according to the conventional publicly-known gene engineering technique. Thus, for example, each of DNA encoding the protein (X), DNA encoding the linker peptide (L) and DNA encoding the protein (A) is amplified if necessary, those DNAs are bound each other, the resulting DNA is inserted into a cellular expression vector and a host cell is transfected with the vector to express the fusion protein whereby fusion protein of the present invention can be manufactured. Amplification of DNA can be conducted by, for example, a PCR method. Binding of the amplified DNA can be conducted, for example, by an overlap extension PCR method. It is also possible to design an amino acid sequence of fusion protein to be expressed so as to directly prepare an artificial synthetic gene. It is preferred that the expression vector includes a promoter such as CMV or SV 40 for enhancing the expression efficiency and a secretion signal sequence such as antibody heavy chain signal sequence or antibody κ chain signal sequence for easy recovery of the expressed fusion protein from culture supernatant. It is also preferred that kozak sequence is inserted into the upper stream of the transcription initiating codon for enhancing the expressed protein amount. In the case of the present fusion protein, nAChRα1 subunit which is a membrane protein exists in N terminal side and, in addition, the present membrane protein has an extracellular region in N terminal side and, accordingly, compatibility of expressed protein and signal sequence is good resulting in good secretion expression when an original signal sequence of nAChRα1 subunit is used. As to the expression host cell, mammalian cell, yeast, animal cell, insect cell, plant cell, bacterial cell (*Escherichia coli* etc.) etc. can be used. Among them, animal cell is preferred and CHO cell, HEK293 cell, etc. are particularly preferred. Further, when a nucleic acid sequence which expresses the fusion protein is infused into chromosomes, expression as a transgenic animal is also possible. The expressed fusion protein may be recovered by conventional means and may be purified by, for example, means of a Protein A column method.

Now, illustrations will be made to the composition for prevention and treatment of autoimmune disease of autoantibody type characterized by comprising the fusion protein of the present invention as an effective ingredient. Examples of the specific preparation form of such a composition are injection and mucosal absorber. In the case of injection, a stabilizer such as saccharide, polyol, albumin or surfactant, an isotonization agent such as salt, etc. are added to the above-prepared fusion protein of the present invention, the resulting product is freeze-dried for preservation and administered by dissolving in water for injection upon use. Although there is no particular limitation for the content of the fusion protein of the present invention in the freeze-dried product, it is 0.01 to 200 mg/g and preferably 0.1 to 100 mg/g, for example. Although there is no particular limitation for the content of the fusion protein in the dissolved injection, it is 0.01 to 200 mg/mL and preferably 0.1 to 100 mg/mL, for example. Examples of the administering method in the case of injection include intravenous administration, intramuscular administration and subcutaneous administration. In the case of mucosal absorber, the fusion protein of the present invention is made into a dosage form together, for example, with excipient and stabilizer so as to give a sustained-release mucosal absorber preparation and it may be administered via oral mucosa, nasal mucosa, eyelid, etc. Although there is no particular limitation for the content of the fusion protein of the present invention in the mucosal absorber, it is 0.1 to 300 mg/ml, and preferably 0.5 to 100 mg/mL, for example. Dose of the composition of the present invention varies depending upon the aimed therapeutic effect, administering method, therapeutic period, age, body weight, etc. and it is usually 10 μg/kg to 50 mg/kg per day for an adult.

EXAMPLES

The present invention will now be illustrated in more detail as hereunder by Examples, but the present invention is not limited to these Examples.

(1) Construction of Expression Vector of α1-Fc Fusion Protein (Comparative Example)

Sequence of signal sequence and N-terminal extracellular region was extracted from nAChRα1 subunit based on isoform 1 protein sequence information (Accession No. P02708-2) of already-known nicotinic acetylcholine receptor (nAChR) α1 subunit. Sequence of Fc region was also extracted based on protein sequence information (Accession No. P01857) of human antibody IgG1 constant region. After that, protein sequence of 462 residues was designed wherein both sequences were fused.

In order to conduct the expression of fusion protein using Chinese hamster ovary cells (CHO cells), optimization to nucleic acid sequence suitable for CHO cells was conducted and a nucleic acid sequence was prepared wherein restriction enzyme recognition sequence and kozak sequence were added to the 5' side while termination codon and restriction enzyme recognition sequence were added to 3' side by means of an artificial gene synthetic technique (SEQ ID NO:1).

The resulting artificial synthetic gene was treated with restriction enzyme and inserted under the domination of hCMV-MIE promoter of pEE12.4 which was an expression vector for animal cells to construct a vector pEE12.4-A1Fc for secretion and expression of fusion protein α1-Fc (SEQ ID NO:2) comprising N-terminal extracellular region of isoform 1 of human nAChRα1 subunit and human antibody IgG1 heavy chain Fc region. Scheme of the protein expression region is shown in FIG. 1.

(2) Construction of Expression Vector of α1-L-Fc Fusion Protein (Example of the present invention)

Nucleic acid amplification was conducted for nAChRα1 subunit region containing the kozak sequence of SEQ ID NO:1 by PCR method using the artificial synthetic gene prepared in (1) as a template; using a primer of SEQ ID NO:3 and a primer of SEQ ID NO:4 to which nucleic acid sequence encoding a flexible linker (L) (Pro-(Gly-Gly-Gly-Gly-Ser)3) were added as a primer set; and using "KOD-Plus-Neo" (catalog No.: KOD-401) of Toyobo as a DNA polymerase whereupon a nucleic acid sequence of SEQ ID NO:5 was prepared.

On the other hand, nucleic acid amplification was conducted for the antibody IgG1 Fc region by PCR method using the artificial synthetic gene of SEQ ID NO:1 as a template; using a primer of SEQ ID NO:6 to which a nucleic acid sequence encoding a flexible linker sequence was added and a primer of SEQ ID NO:7 as a primer set; and using KOD-Plus-Neo of Toyobo as a DNA polymerase whereupon a nucleic acid sequence of SEQ ID NO:8 was prepared.

Nucleic acid amplification was conducted by overlap extension PCR method using a mixed solutions of SEQ ID NO:5 and SEQ ID NO:8 as a template; using a primer of SEQ ID NO:3 and a primer of SEQ ID NO:7 as a primer set; and using KOD-Plus-Neo of Toyobo as a DNA polymerase whereupon a nucleic acid sequence of SEQ ID NO:9 was prepared.

Figure 2:
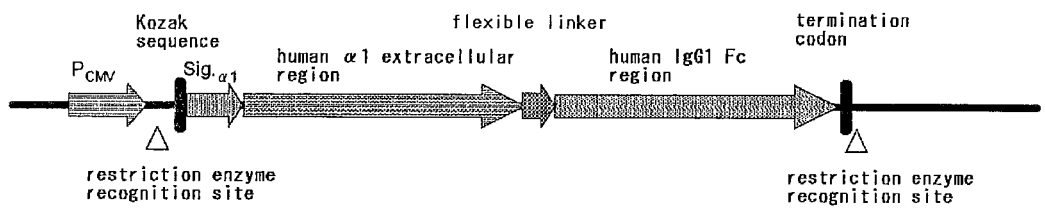
FIG. 2 is a schematic chart of region for expressing a fusion protein α1-L-Fc prepared in Examples.

The resulting amplified product of nucleic acid was treated with restriction enzyme and inserted under domination of hCMV-MIE promoter of pEE12.4 which was an expression vector for animal cells to construct a vector pEE12.4-A1LFc for secretion and expression of fusion protein α1-L-Fc (SEQ ID NO:10) wherein N-terminal extracellular region of isoform 1 of human nAChR.alpha.1 subunit and human antibody IgG1 heavy chain Fc region were connected by a flexible linker sequence (L). Scheme of the protein expression region is shown in FIG. 2.

(3) Confirmation of Transient Expression of Fusion Protein α1-Fc and Fusion Protein α1-L-Fc HEK293 cells were transfected with fusion protein expression vectors pEE12.4-A1Fc and pEE12.4-A1LFc prepared in (1) and (2) using an expression system "Free Style MAX 293 Expression System" (catalog No. K9000-10) of Invitrogen to express the fusion protein α1-Fc and the fusion protein α1-L-Fc. Then they were purified using a purifying column "HiTrap Protein A HP Column" (catalog No. 17-0402-01) of GE Health Care to give the fusion protein α1-Fc and the fusion protein α1-L-Fc.

Figure 5:
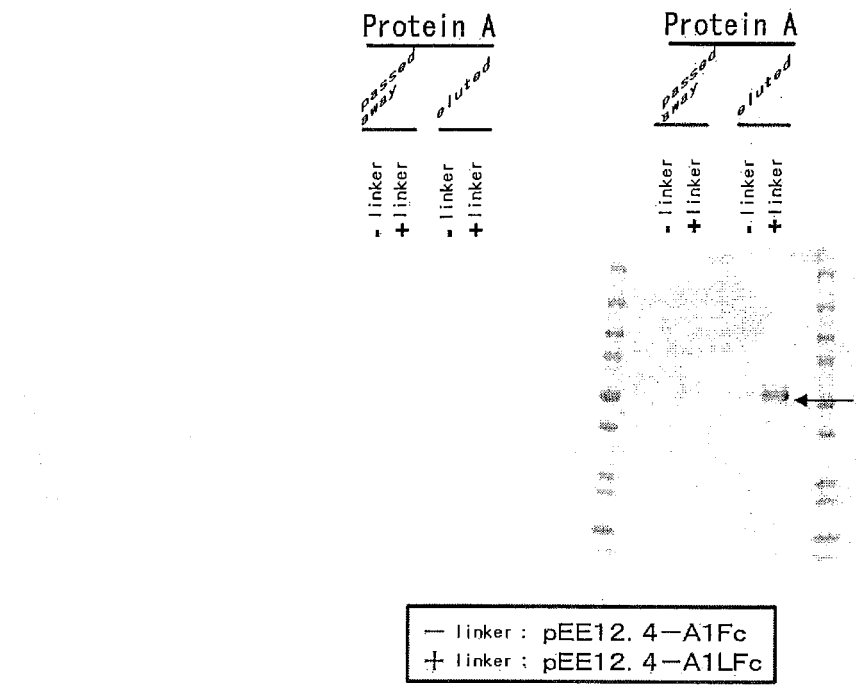
FIG. 5 shows a silver-stained image (left side) and a western blotting image (right side) after SDS-PAGE of fusion protein α1-Fc and fusion protein α1-L-Fc in a reduced state purified after a transient expression.

Confirmation of expression of each of the fusion protein was conducted by means of a silver staining and a western blotting after SDS-PAGE. For the western blotting, an HRP-labeled anti-human IgG antibody was used. The result is shown in FIG. 5. A band shown by an arrow in FIG. 5 corresponds to the fusion protein. From this result, it was confirmed that, when a flexible linker (L) was inserted, expressed amount of fusion protein significantly increased.

(4) Construction of Expression Vector of α1-L2-Fc Fusion Protein (Example of the Present Invention)

There was prepared a vector for expressing a fusion protein α1-L2-Fc ( SEQ ID NO:15) wherein a flexible liner (L) (Pro-(Gly-Gly-Gly-Gly-Ser)3) of α1-L-Fc prepared in (2) was modified to a flexible linker (L2) ((Gly-Gly-Gly-Gly-Ser)3).

Preparation of gene sequence encoding fusion protein (SEQ ID NO:18) was conducted by the same PCR method wherein an artificial synthetic gene ( SEQ ID NO:1) was used as a template and the primers of SEQ ID NOs:4 and 6 of (2) were substituted with SEQ ID NOs:16 and 17.

Figure 3:
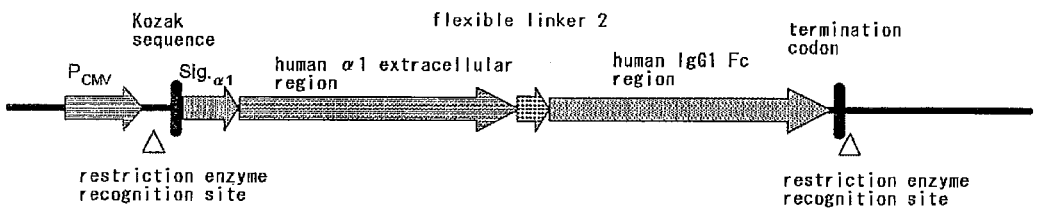
FIG. 3 is a schematic chart of region for expressing a fusion protein α1-L2-Fc prepared in Examples.

The resulting amplified product of nucleic acid was treated with restriction enzyme and inserted under domination of hCMV-MIE promoter of pEE12.4 which was an expression vector for animal cells to construct a vector pEE12.4-A1L2Fc for secretion and expression of fusion protein α1-L2-Fc wherein N-terminal extracellular region of isoform 1 of human nAChRα1 subunit and human antibody IgG1 heavy chain Fc region were connected by a flexible linker sequence (L2). Scheme of the protein expression region is shown in FIG. 3.

(5) Construction of Expression Vector of Fc-L2-α1 Fusion Protein (Comparative Example)

There was prepared a vector for expressing a fusion protein Fc-L2-α1 ( SEQ ID NO:19) wherein nAChRα1 subunit of α1-L2-Fc prepared in (4) and antibody heavy chain constant region were fused in a reversed order to (4) sandwiching a flexible linker (L2).

Preparation of the vector was conducted by PCR method in the same manner as in (2) and (4) using artificial synthetic gene of SEQ ID NO:1 as a template.

Figure 4:
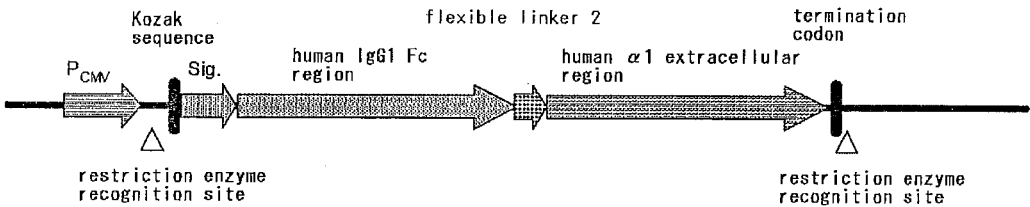
FIG. 4 is a schematic chart of region for expressing a fusion protein Fc-L2-α1 prepared in Examples.

The resulting amplified product of nucleic acid was treated with restriction enzyme and inserted under domination of hCMV-MIE promoter of pEE12.4 which was an expression vector for animal cells to construct a vector pEE12.4-FcL2A1 for secretion and expression of fusion protein Fc-L2-α1 wherein human antibody IgG1 heavy chain Fc region and N-terminal extracellular region of isoform 1 of human nAChRα1 subunit were connected by a flexible linker sequence (L2). Scheme of the protein expression region is shown in FIG. 4.

(6) Construction of Stable Expression Strains of Fusion Proteins α1-Fc, α1-L-Fc, α1-L2-Fc, and Fc-L-α1

Each of fusion protein expression vectors pEE12.4-A1Fc, pEE12.4-A1LFc, pEE12.4-A1L2Fc, and pEE12.4-FcL2A1 prepared in (1), (2), (4) and (5) was transferred into CHO-K1 cells by an electroporation method, incubated under methionine sulfoximine (MSX) selection and cloned to prepare a transformant. The resulting transformants (hereinafter, each of them will be abbreviated as "α1-Fc expression cell", "α1-L-Fc expression cell", "α1-L2-Fc expression cell", and "Fc-L2-α1 expression cell") was subjected to the following experiment.

(7) Expression Incubation of Fusion Proteins α1-Fc, α1-L-Fc, α1-L2-Fc, and Fc-L2-α1

Each of α1-Fc expression cells, α1-L-Fc expression cells, α1-L2-Fc expression cells, and Fc-L2-α1 expression cells prepared in (6) were incubated using 9 L of "CD-CHO medium" (catalog No. 12490-025) of Invitrogen as an incipient medium so as to produce each protein. The incubating condition was pH 7.1 at 37° C. and, during the fifth to the ninth days of the incubation, 50 mL/L/day of "CHO CD EfficientFeed B" (catalog No. A1024-01) of Invitrogen was added and incubation was conducted for 10 days. Supernatant liquid of the fusion protein expression culture was obtained by centrifuging the culture at 3500×G for 5 minutes to precipitate the incubated cells and recovering the supernatant liquid therefrom.

(8) Purification of Fusion Proteins α1-Fc, α1-L-Fc, α1-L2-Fc, and Fc-L2-α1 and Calculation of Expressed Amount For each supernatant liquid of the fusion protein expression culture obtained in (7), a solution after a filtering treatment with a filter of 0.45 μm was loaded to "Mab select SuRe" (catalog No. 11-0026-01) of GE Healthcare, washed with PBS of 10-column volume and eluted with 2.5-column volume of 20 mM citric acid buffer (pH=3.0) and the eluate was immediately neutralized with 1M Tris-HCl (pH=9.0) in an amount of one-tenth of the eluate to purify the fusion protein. The resulting eluate was concentrated using "Amicon Ultra-15, Ultracel-50K" (catalog No. UFC905024) of Japan Millipore, substitution with PBS was conducted and a filtering treatment was done using an aseptic filter membrane of 0.22 μm followed by subjecting to the following experiment.

Absorbance at 280 nm (OD280) of the resulting eluate fraction was measured and expressed amount of fusion protein per 1 L of the incubated liquid for each expression strain was calculated using absorption coefficient (α1-Fc:0.57 mg/mL/OD280, α1-L-Fc:0.59 mg/mL/OD280, α1-L2-Fc: 0.59 mg/mL/OD280, Fc-L2-α1:0.59 mg/mL/OD280) of each fusion protein, eluate amount and incubated liquid amount.

The result was that the expressed amount of fusion protein was 72 mg/L for α1-Fc expression cells, 1587 mg/L for α1-L-Fc expression cells, 1249 mg/L for α1-L2-Fc expression cells, and 356 mg/L for Fc-L2-α1 expression cells, and it was confirmed that the expressed amount was significantly enhanced by insertion of flexible linker peptide into the binding site of the fusion protein. Among them, a fusion protein expression strain using Pro-(Gly-Gly-Gly-Gly-Ser)3 as a flexible peptide linker was excellent.

(9) Confirmation of Binding Ability of Fusion Protein α1-Fc and Fusion Protein α1-L-Fc to α-BTX With regard to the fusion protein α1-Fc and the fusion protein α1-L-Fc obtained in (8), the binding ability thereof to α-bungarotoxin (hereinafter, it will be abbreviated as "α-BTX") and to Protein A was confirmed with a method of ELISA. α-BTX is a substance having an action of inhibiting the neurotransmission by binding to α1 domain. Accordingly, as a result of confirmation of the binding ability of fusion protein to α-BTX, it is now possible to confirm whether the structure of α1 domain of the fusion protein is correctly formed. Further, Protein A fixes the fusion protein to a plate via Fc. Accordingly, although the main purpose of this experiment is to confirm the formation of α1 domain structure of fusion protein as mentioned above, it is also possible in this experiment to confirm whether the structure of fusion protein as an Fc is retained.

"Protein A" (catalog No. 987015) of ICN Biochemicals was immobilized at the concentration of 1 μg/mL in "C8 Maxisorp Nunc-Immuno Module" (catalog No. 445101) of Nalge Nunc and then blocking was conducted using PBS to which 1% of BSA was added, each of the fusion proteins prepared in (8) and subjected to 4-fold dilution series was added thereto as a sample followed by further washing, then "α-bungarotoxin, biotin-XX" (catalog No. B 1196) of Invitrogen was added at the concentration of 1 μg/mL and, finally, reaction was conducted with "Peroxidase-Avidin" (catalog No. 191370) of ICN Biochemicals. For the detection, "TMB solution" (catalog No. N301) of Funakoshi was made to react as a substrate and the reaction was stopped using 1% sulfuric acid solution. After that, absorbance at 450 nm wavelength was measured.

Figure 6:
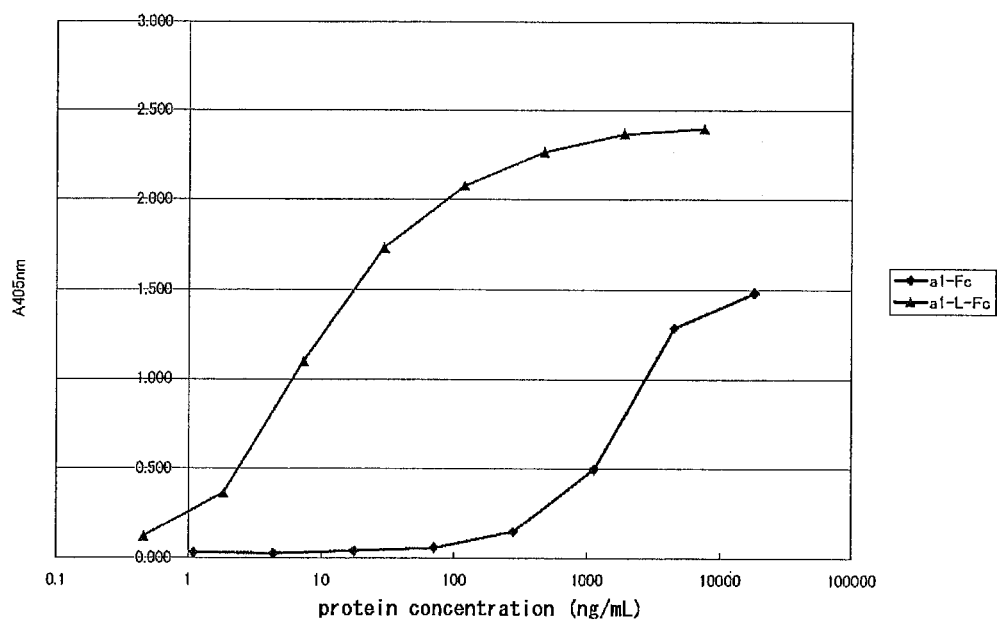
FIG. 6 shows a binding ability of fusion protein α1-Fc and fusion protein α1-L-Fc to Protein A and α-bungarotoxin. ♦ shows the result for the fusion protein α1-Fc and ▲ shows the result for the fusion protein α1-L-Fc.

The result is shown in FIG. 6. For any of the fusion proteins, concentration-dependent reaction was noted. From this result, it was confirmed that each fusion protein binds to α-BTX and also binds to Protein A. Thus, it was confirmed that both of the fusion protein α1-Fc and the fusion protein α1-L-Fc retained the nAChRα1 subunit extracellular region and the structure as Fc. Incidentally, when both fusion proteins were compared, a binding curve to α-BTX was significantly shifted to a lower concentration side in the fusion protein α1-L-Fc whereby it was judged that, when flexible linker peptide is inserted, binding ability per protein concentration is enhanced to an extent of about 100-fold or more. This result suggests that, when flexible linker peptide is inserted, structural stability of the aimed fusion protein increases and purity becomes high.

(10) Confirmation of Binding Ability of Fusion Protein α1-Fc and Fusion Protein α1-L-Fc to Anti-nAChR Autoantibody Mab35 (TIB-175) (hereinafter, it will be abbreviated as "Mab35 cells") which is rat anti-nAChR (α1 subunit) autoantibody production hybridoma obtained from ATCC was incubated in "Hybridoma-SFM" (catalog No. 12045-01) of Invitrogen and the supernatant liquid of the culture was treated with "HiTrap Protein G HP Column" (catalog No. 17-0405-01) of GE Healthcare whereupon a monoclonal antibody (hereinafter, it will be abbreviated as "mAb35") which is an anti-nAChR autoantibody was obtained.

The resulting mAb35 was immobilized at the concentration of 1 μg/mL in C8 Maxisorp Nunc-Immunomodule of Nalge Nunc and blocked using PBS to which 1% of BSA was added. After that, the fusion protein α1-Fc and the fusion protein α1-L-Fc prepared in (8) and subjected to 4-fold dilution series were added and, finally, reaction was conducted using HRP-labeled anti-human IgG1 Fc antibody. For the detection, "TMB solution" of Funakoshi was made to react as a substrate and the reaction was stopped using 1% sulfuric acid solution. After that, absorbance at 450 nm wavelength was measured.

Figure 7:
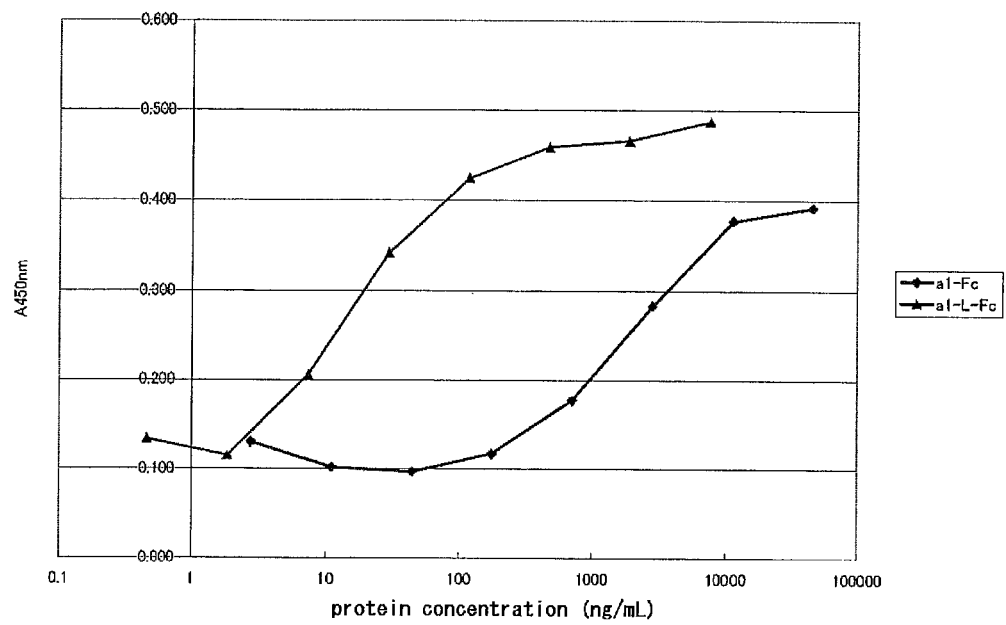
FIG. 7 shows the binding ability of fusion protein α1-Fc and fusion protein α1-L-Fc to anti-nAChRα1 subunit autoantibodies. ♦ shows the result for the fusion protein α1-Fc and ▲ shows the result for the fusion protein α1-L-Fc.

The result is shown in FIG. 7. Both of the fusion protein α1-Fc and the fusion protein α1-L-Fc showed a concentration-dependent reaction. When both were compared, a binding curve to autoantibody was significantly shifted to lower concentration side in the fusion protein α1-L-Fc whereby it was judged that, when flexible linker peptide is inserted, binding ability (specific activity) per protein concentration is enhanced to an extent of about 100-fold or more. This result suggests that, when flexible linker peptide is internally inserted, not only the expressed amount of the aimed fusion protein but also the structural stability thereof increase and the reactivity with autoantibody is significantly enhanced.

(11) Confirmation of Binding Ability of Fusion Protein α1-Fc and Fusion Protein α1-L-Fc to Autoantibody Production Cells In a living body, autoantibodies are produced in B cells. On the cell membrane of the cell surface of the autoantibody production B cells, the same antibodies as the autoantibodies are presented as a B cell receptor. Thus, on the cell membrane of the hybridoma Mab35 used in (10), it is likely that the hybridoma Mab35 also presents mAb35 antibody the same as in the case of B cells.

Now, $2 \times 10^5$ Mab35 cells washed with HBSS/BSA were made to react with each of the fusion protein α1-Fc and the fusion protein α1-L-Fc prepared in (8) diluted to 10-fold within a range of 10 ng/mL to 1 mg/mL as samples. After that, PE-labeled anti-human IgG antibody was added as a detection reagent and the detection was conducted using "Cytomice FC500" of Beckman-Coulter.

Figure 8A:
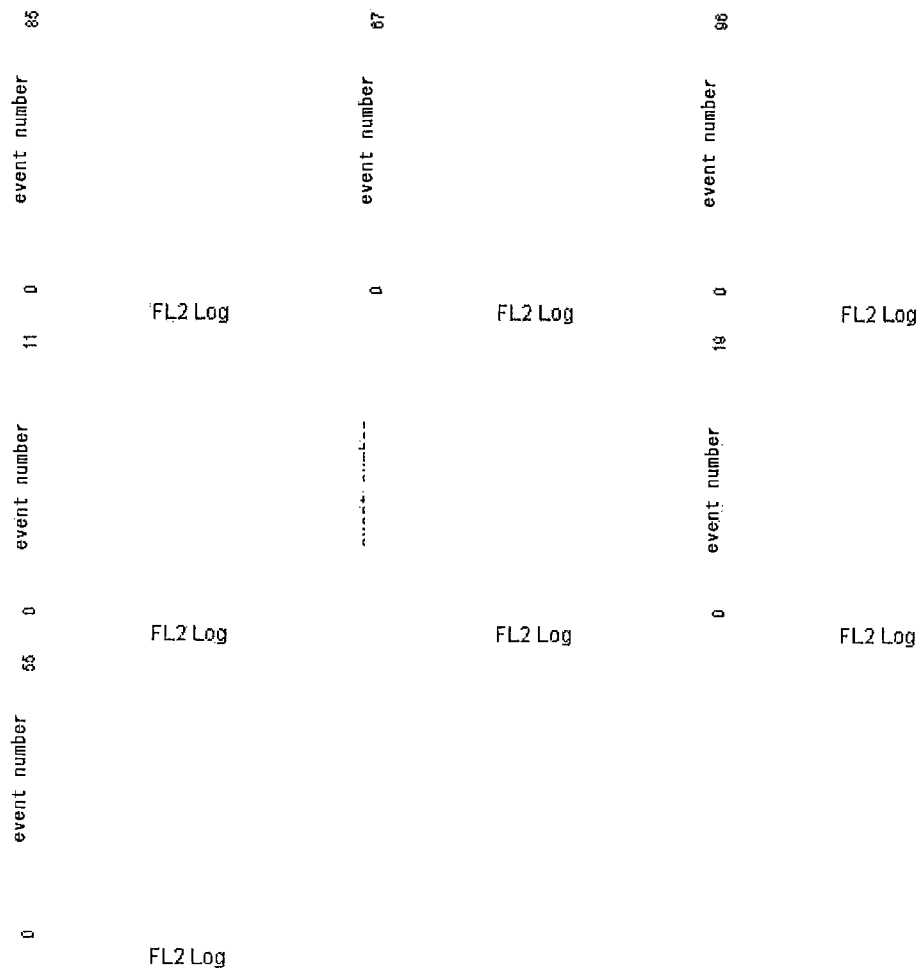
FIG. 8A shows a binding of fusion protein α1-Fc to hybridoma Mab35 cells. Added concentration of the fusion protein is shown in FIG. 8A.
Figure 8B:
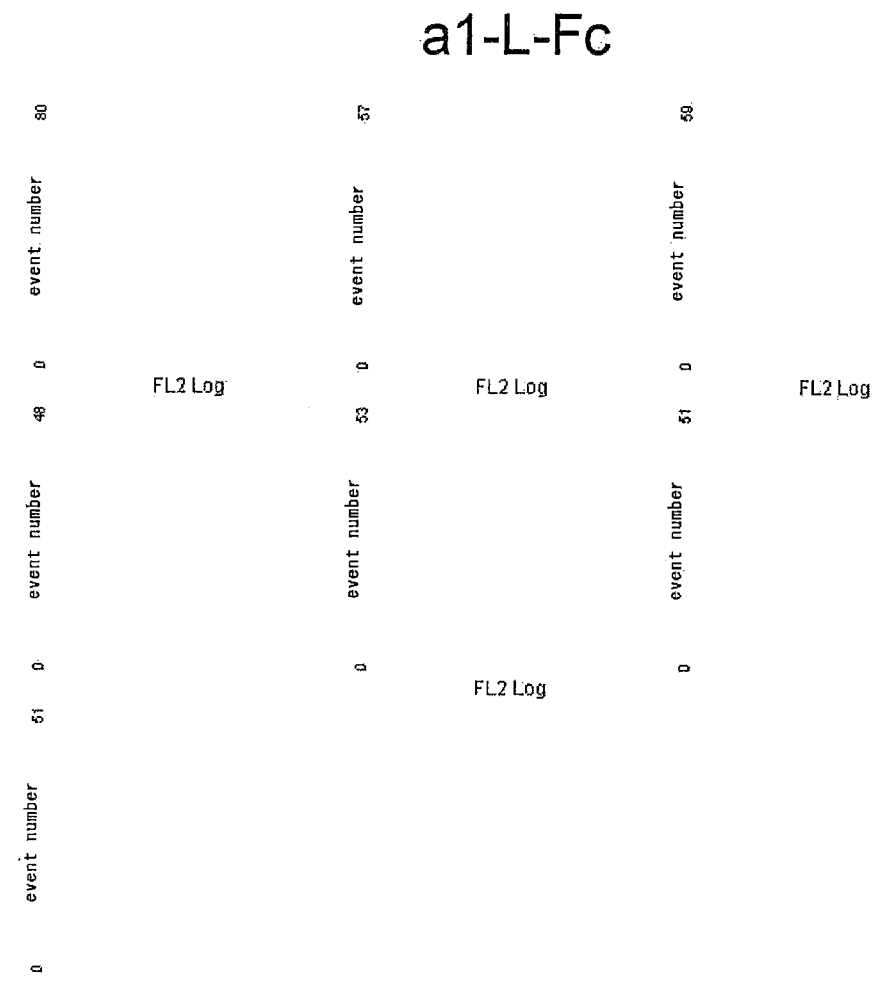

The result is shown in FIG. 8A and FIG. 8B. Each of the fusion proteins was shifted to the right side in a concentration-dependent manner whereby it was confirmed that each of the fusion proteins binds to Mab35 cells in a concentration-dependent manner. Since the fusion protein α1-L-Fc was much more shifted, it was confirmed that, when flexible linker peptide is inserted, the binding ability to autoantibody production cells is enhanced to an extent of about 100-fold or more.

(12) Confirmation of Action of Fusion Protein α1-Fc and Fusion Protein α1-L-Fc as Decoy nAChRα1 subunit similar to human muscle cells is present in the human neuroblastoma cells (TE-671) (hereinafter, it will be abbreviated as "TE671 cells") obtained from ATCC. Therefore, a binding-inhibitive activity of the fusion protein α1-Fc and the fusion protein α1-L-Fc prepared in (8) to the bond of the autoantibody mAb35 to TE671 cells was confirmed.

To $2 \times 10^5$ TE671 cells washed with HBSS/BSA was added 100 μg/mL of the fusion protein α1-Fc or the fusion protein α1-L-Fc. As to a control, HBSS/BSA containing no fusion protein was added. After 1 μg/mL of mAb35 antibody was further added thereto, PE-labeled rat IgG antibody was added as a detection reagent and the detection was conducted using "Cytomics FC 500".

Figure 9:
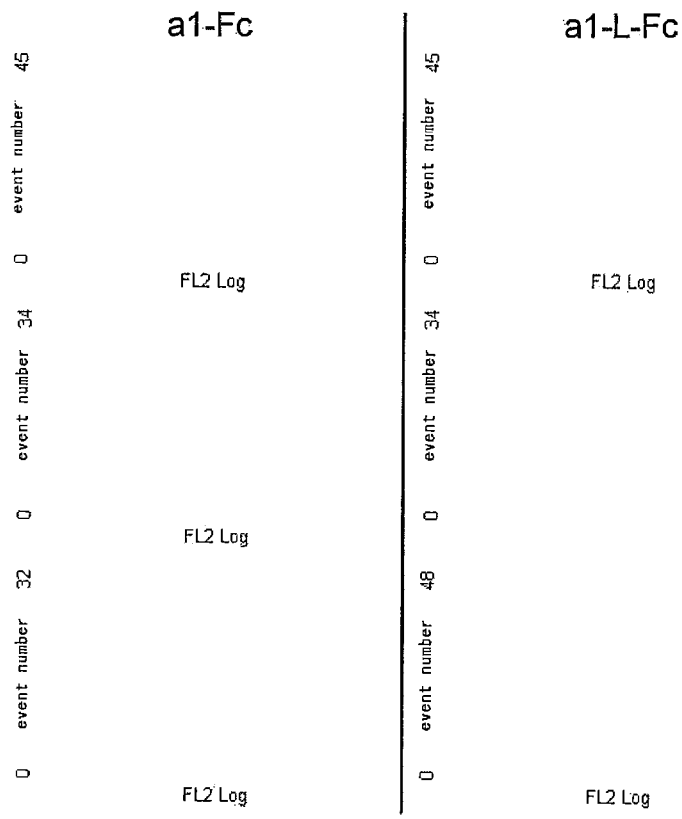
FIG. 9 shows a binding inhibitive activity of 100 μg/mL of fusion protein α1-Fc (left side) and a binding inhibitive activity of fusion protein α1-L-Fc in the same concentration (right side) to the binding of 1 μg/mL of autoantibody mAb35 to TE671 cells.

The result is shown in FIG. 9. When the fusion protein α1-Fc was used, only some inhibiting effect was noted at the concentration of 100 μg/mL while, when the fusion protein α1-L-Fc was used, sufficient inhibiting effect was noted at the concentration of 100 μg/mL. From this result, a significant enhancement of inhibiting activity by internal insertion of flexible linker peptide was confirmed.

(13) Confirmation of ADCC Activity of Fusion Protein α1-Fc, Fusion Protein α1-L-Fc, and Fusion Protein Fc-L2-α1

Mab35 cell ($2 \times 10^5$ cells) was washed with HBSS/BSA and incubated at 37° C. for 30 minutes in HBSS/BSA to which a fluorescent dye "Calcein-AM" (catalog No. C326) of Dojinsha was added to make the concentration 10 μM whereby Calcein-AM was incorporated into the cells. After that, those Mab35 cells were disseminated to a 96-well plate to make 10000 cells per well and then the fusion protein α1-L-Fc prepared in (8) or a control antibody (Avastin or Enbrel) and human natural killer NK92 cells (CRL-2407) obtained from ATCC (hereinafter, it will be abbreviated as "NK92 cells") were added thereto in various concentrations followed by incubating at 37° C. for 4 hours. After the incubation, centrifugal separation was conducted at 300×G for 5 minutes to precipitate the cells and fluorescence of each supernatant liquid was measured (Ex=485 nm, Em=540 nm). As a result, although a very weak cellular cytotoxicity (natural killing) was noted in a dependently manner on NK92 cell numbers even in a group wherein only NK92 cells were added (no antibody, etc. added), a strong cellular cytotoxicity of about 73% at the highest was noted in a group wherein the fusion protein α1-L-Fc was administered, and a strong cellular cytotoxicity was noted in a group wherein 25-fold amount of NK92 cells (i.e. the effector cells (E)) were added to Mab35 cells (i.e. the target cells (T)) (no data shown). From the result of the above preliminary experiments, cellular cytotoxicity was compared among the fusion protein α1-Fc, the fusion protein α1-L-Fc and the fusion protein Fc-L2-α1 under the condition wherein E/T ratio was 25.

As a result, cellular cytotoxicity values of 51.8%, 73.2% and 32.9% were noted in the fusion protein α1-Fc, in the fusion protein α1-L-Fc and in the fusion protein Fc-L2-α1, respectively. On the other hand, cellular cytotoxicity values of 17.9%, 12.5% and 6.9% were noted in a group wherein no antibody was added, in an Avastin-added group and in an Enbrel-added group, respectively.

From those results, it was confirmed that higher cytotoxicity was exhibited when the antibody heavy chain constant region was not positioned at N terminal side but was positioned at C terminal side. It was also confirmed that cellular cytotoxicity was further enhanced by internal insertion of flexible linker peptide even in the case wherein antibody heavy chain constant region was positioned at C terminal side.

(14) Confirmation of In Vivo Test to Myasthenia Gravis

For the experiment, 36 female Lewis rats of 11 weeks age (Nippon LSC) were prepared. As an animal model for myasthenia gravis, an autoantibody-inducing rat model was used. mAb35 which is an autoantiboy to the rat nAChR produced by hybridoma Mab35 was intraperitoneally administered to all rats in a dose of 1.25 mg/kg whereupon a morbid state was induced. Each of the following substances was intravenously administered after 4, 12, 24 and 32 hours from the administration of mAb35. To a control group, 1 mL of PBS was administered for each time (control group, 6 rats). α1-L-Fc prepared in (8) was administered at the dose of 2.5 mg/rat (α1-L-Fc 2.5, 6 rats) or 10 mg/rat (α1-L-Fc 10, 6 rats) for each time. Similarly, α1-Fc prepared in (8) was administered at the dose of 2.5 mg/rat (α1-Fc 2.5, 6 rats) or 10 mg/rat (α1-Fc 10, 6 rats) for each time. Further, donated Venoglobulin IH 5% for intravenous injection (manufactured by Tanabe Mitsubishi) which was a human immunoglobulin preparation for intravenous injection was administered at the dose of 80 mg/rat (IVIG, 6 rats) for each time.

During the period until 96 hours after induction of morbid state, muscle symptom score (MG Score) was evaluated. The muscle symptom score is as follows: point 0 for no abnormality; point 1 for lowering in grip of forelimbs; point 2 for disappearance of grip of forelimbs; point 3 for lowering of muscle strength of hind limbs and gait disorder in addition to disappearance of grip of forelimbs; and point 4 for paralysis of hind limbs in addition to disappearance of grip of forelimbs. Statistic analysis of the muscle symptom score was conducted in such a manner that comparison of the control group with each substance-administered group was done by Steel test (SAS Preclinical Package Version 5.00.010720, Windows (registered trade mark) version, SAS System Release 8.02 TS Level 02M0 (SAS Institute Japan)). The result is given in terms of (mean value)±(standard error) and the significance level of less than 5% (*) was judged as significant difference.

Figure 10:
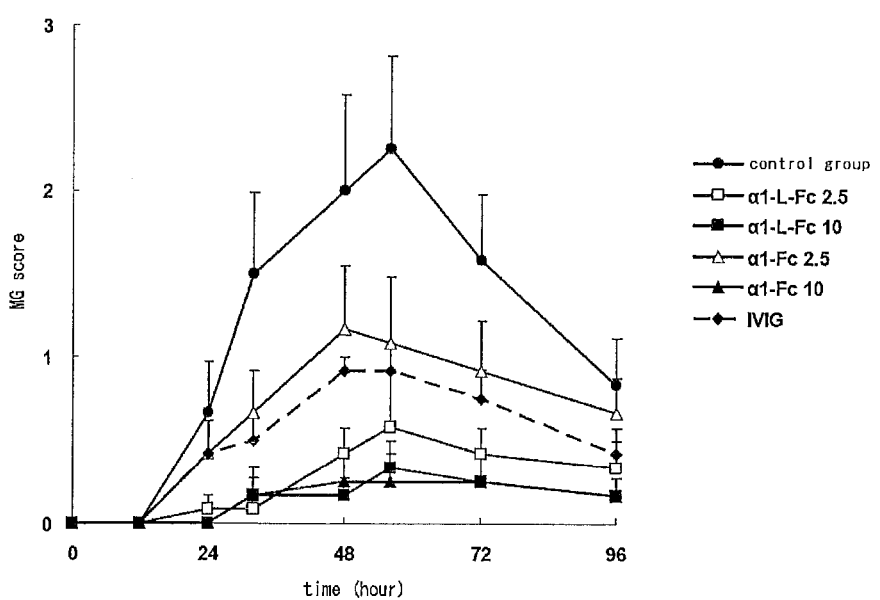
FIG. 10 shows an improving effect of fusion protein α1-Fc and fusion protein α1-L-Fc to myasthenia gravis-like symptom induced by autoantibody mAb35. The abscissa shows time and the ordinate shows score of myasthenia gravis-like symptom. ● shows a group administered with physiological saline, ◆ shows a group administered with a globulin preparation for intravenous injection, Δ and ▲ each shows a group administered with fusion protein α1-Fc, and □ and ■ each shows a group administered with fusion protein α1-L-Fc.

The result is shown in Table 1 and FIG. 10. FIG. 10 shows the effect of α1-L-Fc and α1-Fc in the mAb35-induced rat myasthenia gravis model. As shown in FIG. 10, such a change was observed in the control group that the muscle symptom score increased as from 24 hours after induction of morbid state, became highest after 56 hours and decreased thereafter. There was shown such a tendency that α1-L-Fc and α1-Fc suppressed the increase of the muscle symptom score and that the suppression as such is dependent on the dose. Table 1 shows a mean score after 56 hours from morbid state induction wherein the muscle symptom score of the control group became highest. It was shown that any of α1-L-Fc and α1-Fc significantly suppressed the muscle symptom by administration of 10 mg/rat for each time.

TABLE 1

| muscle symptom score after 56 hours from morbid state induction | |
|---|---|
| | muscle symptom score |
| control | 2.3 ± 0.6 |
| α1-L-Fc 2.5 | 0.6 ± 0.3 |
| α1-L-Fc 10 | 0.3 ± 0.2* |
| α1-Fc 2.5 | 1.1 ± 0.4 |
| α1-Fc 10 | 0.3 ± 0.2* |
| IVIG | 0.9 ± 0.2 |

In the above Examples, the effect was confirmed for the cases wherein a linker peptide having repetition number of 3 (flexible linker (L) (Pro-(Gly-Gly-Gly-Gly-Ser)3) or flexible linker (L2) ((Gly-Gly-Gly-Gly-Ser)3)) was used. From those results, persons skilled in the art can easily predict that even the cases wherein repeating number (n) of the linker peptide is integer of 1 to 8 or, particularly, integer of 1 to 4 will achieve the same excellent effect as the cases wherein the repetition number (n) of the linker peptide is 3. That is because the length of a linker peptide has been said to be usually from about 5 residues (in other words, the repetition number (n) in the above constitution unit is 1) to about 20 residues (in other words, the repetition number (n) in the above constitution unit is 4).

INDUSTRIAL APPLICABILITY

In accordance with the present invention, the fusion protein, which can prevent or treat the autoimmune disease of autoantibody type by two ways (i.e. inhibition of the autoantibody production and neutralization of the produced autoantibodies), can be provided as a drug in an actual production scale. Therefore, the fusion protein of the present invention can be widely used for effectively preventing and treating various autoimmune diseases of autoantibody type such as myasthenia gravis.

Sequence Listing Free Text

Sequence ID Nos. 3, 4, 6, 7, 16 and 17 are the sequences of the primers.

The invention claimed is:

1. A fusion protein, comprising
   (a) protein (X), wherein protein (X) is isoform 1 or isoform 2 of human nAChRα1 subunit, or a ligand-binding portion thereof,
   (b) protein (A), wherein protein (A) is a human antibody heavy chain constant region, or a portion thereof having cytotoxic activity, and
   (c) a linker peptide (L) consisting of an amino acid sequence represented by the formula (Gly-Gly-Gly-Gly-Ser)n (SEQ ID NO: 22) (in the formula, n is an integer of 1 to 4), or the formula Pro-(Gly-Gly-Gly-Gly-Ser)n (SEQ ID NO: 23) (in the formula, n is an integer of 1 to 4),
   wherein protein (X), the linker peptide (L) and protein (A) are connected in this order by means of a peptide bond from N terminal to C terminal.

2. The fusion protein according to claim 1, wherein protein (X) is the N-terminal extracellular region of isoform 1 or isoform 2 of human nAChRα1, or a ligand-binding portion thereof.

3. The fusion protein according to claim 1, wherein protein (X) consists of the amino acid sequence set forth in SEQ ID NO:13 or SEQ ID NO:14, or a ligand-binding portion of SEQ ID NO:13 or SEQ ID NO:14, or an amino acid sequence at least 95% identical to SEQ ID NO:13 or SEQ ID NO:14.

4. The fusion protein according to claim 1, wherein protein (A) is an IgG heavy chain constant region, or a portion thereof having cytotoxic activity.

5. The fusion protein according to claim 4, wherein protein (A) is an IgG heavy chain constant region consisting of the amino acid sequence set forth in SEQ ID NO:11 or SEQ ID NO:12, or a portion thereof having cytotoxic activity, or an amino acid sequence at least 95% identical to SEQ ID NO: 11 or SEQ ID NO:12.

6. The fusion protein according to claim 1, wherein the fusion protein consists of the amino acid sequence set forth in SEQ ID NO:10, or an amino acid sequence at least 95% identical to SEQ ID NO: 10.

7. A composition comprising the fusion protein according to claim 1 and a pharmaceutically acceptable carrier.

8. A method for treating myasthenia gravis in a subject in need thereof, comprising administering to the subject the composition of claim 7.

9. An isolated nucleic acid molecule that encodes a fusion protein with at least 85% amino acid sequence identity to SEQ ID NO: 10, wherein the fusion protein binds an anti-acetylcholine receptor autoantibody.

10. A method for manufacturing a fusion protein, comprising expressing the nucleic acid molecule of claim 9 in a cellular expression vector within a host cell.

* * * * *